(12) United States Patent
Hsiung et al.

(10) Patent No.: US 12,352,692 B2
(45) Date of Patent: *Jul. 8, 2025

(54) DYNAMIC PROCESS END POINT DETECTION

(71) Applicant: VIAVI Solutions Inc., Chandler, AZ (US)

(72) Inventors: ChangMeng Hsiung, Redwood City, CA (US); Lan Sun, Santa Rosa, CA (US); Edward Gooding, Hopewell, NJ (US); Michael Klimek, Santa Rosa, CA (US)

(73) Assignee: VIAVI Solutions Inc., Chandler, AZ (US)

( * ) Notice: Subject to any disclaimer, the term of this patent is extended or adjusted under 35 U.S.C. 154(b) by 154 days.

This patent is subject to a terminal disclaimer.

(21) Appl. No.: 18/163,712

(22) Filed: Feb. 2, 2023

(65) Prior Publication Data

US 2023/0204502 A1  Jun. 29, 2023

Related U.S. Application Data

(63) Continuation-in-part of application No. 17/646,038, filed on Dec. 27, 2021, now Pat. No. 11,860,035.

(Continued)

(51) Int. Cl.
*G01J 3/02*    (2006.01)
*G01N 1/38*    (2006.01)
(Continued)

(52) U.S. Cl.
CPC ........... *G01N 21/3577* (2013.01); *G01N 1/38* (2013.01); *G01N 21/359* (2013.01); *G01N 33/15* (2013.01)

(58) Field of Classification Search
CPC .... G01N 21/3577; G01N 1/38; G01N 21/359; G01N 33/15; G01N 21/65;
(Continued)

(56) References Cited

U.S. PATENT DOCUMENTS 5,966,679 A   10/1999   Snowbarger et al.
6,159,255 A   12/2000   Perkins
(Continued)

FOREIGN PATENT DOCUMENTS

CN   1599889 A     3/2005
CN   105987822 A   10/2016

OTHER PUBLICATIONS

Besseling et al., "An Efficient, Maintenance Free and Approved Method for Spectroscopic Control and Monitoring of Blend Uniformity: The moving F-Test," Journal of Pharmaceutical and Biomedical Analysis, Oct. 10, 2015, vol. 114, pp. 471-481.

(Continued)

*Primary Examiner* — Abdullahi Nur
(74) *Attorney, Agent, or Firm* — Harrity & Harrity, LLP

(57) ABSTRACT

A device may receive spectroscopic data associated with a dynamic process. The device may identify a pseudo steady state end point based on the spectroscopic data. The pseudo steady state end point may indicate an end of a pseudo steady state associated with the dynamic process. The device may identify a reference block and a test block based on the pseudo steady state end point, and may generate a raw detection signal associated with the reference block and a raw detection signal associated with the test block. The device may generate an averaged statistical detection signal based on the raw detection signal associated with the reference block and the raw detection signal associated with the (Continued)

test block, and may determine whether the dynamic process has reached a steady state based on the averaged statistical detection signal.

20 Claims, 18 Drawing Sheets

Related U.S. Application Data

(60) Provisional application No. 63/267,531, filed on Feb. 3, 2022.

(51) Int. Cl.
*G01N 21/3577* (2014.01)
*G01N 21/359* (2014.01)
*G01N 33/15* (2006.01)

(58) Field of Classification Search
CPC ... G01N 2021/1789; G01N 2021/8411; G01N 2201/0221; G01N 2201/1222; G01N 2201/1293
See application file for complete search history.

(56) References Cited

U.S. PATENT DOCUMENTS

| 11,042,128 | B2 | 6/2021 | Mishra et al. |
| 11,860,035 | B2 | 1/2024 | Hsiung et al. |
| 2002/0040284 | A1* | 4/2002 | Junk ............... G05B 23/0229 |
| | | | 702/189 |
| 2003/0175706 | A1 | 9/2003 | Zhang |
| 2004/0137484 | A1 | 7/2004 | Zhang et al. |
| 2019/0236333 | A1 | 8/2019 | Hsiung et al. |
| 2021/0192350 | A1 | 6/2021 | Bolliger et al. |

OTHER PUBLICATIONS

Co-pending U.S. Appl. No. 17/646,038, inventor Hsiung; Chang Meng, filed Dec. 27, 2021.
Extended European Search Report for Application No. EP22158959.1, mailed on Aug. 25, 2022, 9 pages.
Fonteyne et al., "Blend Uniformity Evaluation During Continuous Mixing in a Twin Screw Granulator by in-line Nir Using a Moving F-test", Analytica Chimica Acta, Jul. 25, 2016, vol. 935, pp. 213-223, XP029687913.

* cited by examiner

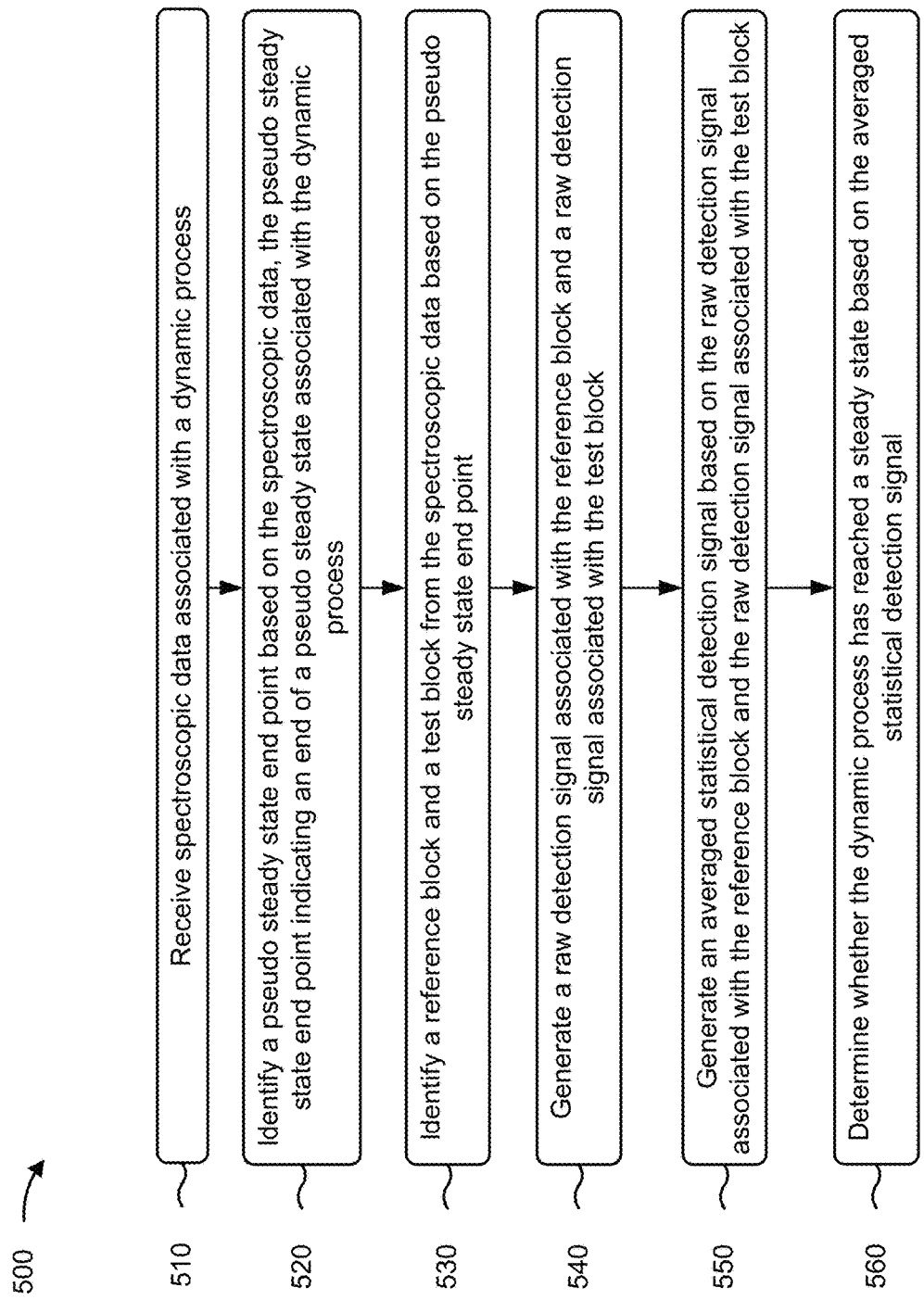

DYNAMIC PROCESS END POINT DETECTION

CROSS-REFERENCE TO RELATED APPLICATIONS

This Patent Application claims priority to U.S. patent application Ser. No. 17/646,038, filed on Dec. 27, 2021, and entitled "BLENDING PROCESS END POINT DETECTION, and to U.S. Provisional Patent Application No. 63/267,531, filed on Feb. 3, 2022, and entitled "BLENDING PROCESS END POINT DETECTION." The disclosures of the prior Applications are considered part of and are incorporated by reference into this Patent Application.

BACKGROUND

A blending process (e.g., a blending process associated with manufacturing a pharmaceutical product) may involve one or more transitions in state, such as a transition from an unsteady state (e.g., a heterogenous state of a blending at which properties of a blend vary with time) to a steady state (e.g., a homogeneous state of blending at which the properties of the blend remain substantially constant with time). For example, a blending process may involve a transition where spectral properties of a blend transition from an unsteady state (e.g., at a start of the blending process) to a steady state (e.g., indicating that the blending process is complete).

SUMMARY

Some implementations described herein relate to a method. The method may include receiving, by a device, spectroscopic data associated with a dynamic process. The method may include identifying, by the device, a pseudo steady state end point based on the spectroscopic data, the pseudo steady state end point indicating an end of a pseudo steady state associated with the dynamic process. The method may include identifying, by the device, a reference block and a test block from the spectroscopic data based on the pseudo steady state end point. The method may include generating, by the device, a raw detection signal associated with the reference block and a raw detection signal associated with the test block. The method may include generating, by the device, a statistical detection signal based on the raw detection signal associated with the reference block and the raw detection signal associated with the test block. The method may include determining, by the device, whether the dynamic process has reached a steady state based on the statistical detection signal.

Some implementations described herein relate to a device. The device may include one or more memories and one or more processors coupled to the one or more memories. The device may be configured to receive spectroscopic data associated with a dynamic process. The device may be configured to identify a pseudo steady state end point based on the spectroscopic data, the pseudo steady state end point indicating an end of a pseudo steady state associated with the dynamic process. The device may be configured to identify a reference block and a test block from the spectroscopic data based on the pseudo steady state end point. The device may be configured to generate a raw detection signal associated with the reference block and a raw detection signal associated with the test block. The device may be configured to generate a statistical detection signal based on the raw detection signal associated with the reference block and the raw detection signal associated with the test block. The device may be configured to determine whether the dynamic process has reached a steady state based on the statistical detection signal.

Some implementations described herein relate to a non-transitory computer-readable medium that stores a set of instructions for a device. The set of instructions, when executed by one or more processors of the device, may cause the device to receive spectroscopic data associated with a dynamic process. The set of instructions, when executed by one or more processors of the device, may cause the device to identify a pseudo steady state end point based on the spectroscopic data, the pseudo steady state end point indicating an end of a pseudo steady state associated with the dynamic process. The set of instructions, when executed by one or more processors of the device, may cause the device to identify a reference block and a test block from the spectroscopic data based on the pseudo steady state end point. The set of instructions, when executed by one or more processors of the device, may cause the device to generate a raw detection signal associated with the reference block and a raw detection signal associated with the test block. The set of instructions, when executed by one or more processors of the device, may cause the device to generate a statistical detection signal based on the raw detection signal associated with the reference block and the raw detection signal associated with the test block. The set of instructions, when executed by one or more processors of the device, may cause the device to determine whether the dynamic process has reached a steady state based on the statistical detection signal.

Some implementations described herein relate to a method. The method may include receiving, by a device, spectroscopic data associated with a dynamic process. The method may include identifying, by the device, a pseudo steady state end point based on the spectroscopic data, the pseudo steady state end point indicating an end of a pseudo steady state associated with the dynamic process. The method may include identifying, by the device, a reference block and a test block from the spectroscopic data based on the pseudo steady state end point. The method may include generating, by the device, a raw detection signal associated with the reference block and a raw detection signal associated with the test block. The method may include generating an averaged statistical detection signal based on the raw detection signal associated with the reference block and the raw detection signal associated with the test block. The method may include determining, by the device, whether the dynamic process has reached a steady state based on the averaged statistical detection signal.

Some implementations described herein relate to a device. The device may include one or more memories and one or more processors coupled to the one or more memories. The one or more processors may be configured to receive spectroscopic data associated with a dynamic process. The one or more processors may be configured to identify a pseudo steady state end point based on the spectroscopic data, the pseudo steady state end point indicating an end of a pseudo steady state associated with the dynamic process. The one or more processors may be configured to identify a reference block and a test block from the spectroscopic data based on the pseudo steady state end point. The one or more processors may be configured to generate a raw detection signal associated with the reference block and a raw detection signal associated with the test block. The one or more processors may be configured to generate an averaged statistical detection signal based on the raw detection signal associated with the reference block and the raw detection signal associated with the test block. The one or more processors may be configured to determine whether the dynamic process has reached a steady state based on the averaged statistical detection signal.

Some implementations described herein relate to a non-transitory computer-readable medium that stores a set of instructions. The set of instructions, when executed by one or more processors of a device, may cause the device to receive spectroscopic data associated with a dynamic process. The set of instructions, when executed by one or more processors of the device, may cause the device to identify a pseudo steady state end point based on the spectroscopic data, the pseudo steady state end point indicating an end of a pseudo steady state associated with the dynamic process. The set of instructions, when executed by one or more processors of the device, may cause the device to identify a reference block and a test block from the spectroscopic data based on the pseudo steady state end point. The set of instructions, when executed by one or more processors of the device, may cause the device to generate a raw detection signal associated with the reference block and a raw detection signal associated with the test block. The set of instructions, when executed by one or more processors of the device, may cause the device to generate an averaged statistical detection signal based on the raw detection signal associated with the reference block and the raw detection signal associated with the test block. The set of instructions, when executed by one or more processors of the device, may cause the device to determine whether the dynamic process has reached a steady state based on the averaged statistical detection signal.

BRIEF DESCRIPTION OF THE DRAWINGS

FIGS. 4 and 5 are flowcharts of example processes relating to dynamic process end point detection, as described herein.

DETAILED DESCRIPTION

Figure 1A:
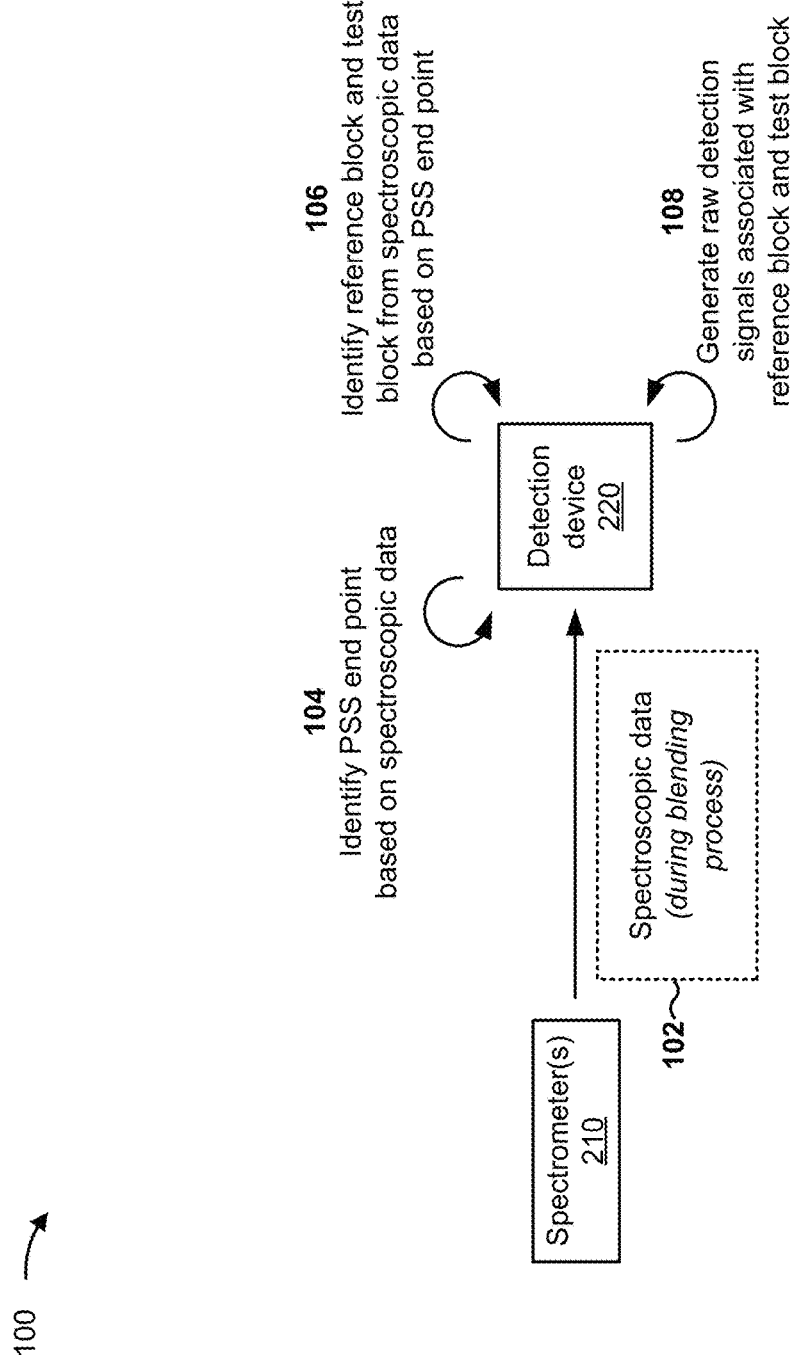
FIGS. 1A-1N are diagrams associated with an example implementation of dynamic process end point detection, as described herein.

The following detailed description of example implementations refers to the accompanying drawings. The same reference numbers in different drawings may identify the same or similar elements. The following description uses a spectrometer as an example. However, the techniques, principles, procedures, and methods described herein may be used with any sensor, including but not limited to other optical sensors and spectral sensors.

Blend homogeneity (sometimes referred to as blend uniformity) of a compound resulting from a blending process (e.g., a blending process used in association with manufacturing a pharmaceutical product) should be monitored to ensure quality and performance of the blending process. Achieving an acceptable blend homogeneity may enable, for example, the compound to be effectively utilized at a later process step or to be provided to a consumer. Conversely, a poor blend homogeneity can result in a compound that is unusable or rejected, meaning that resources dedicated to the blending process would be wasted.

As noted above, a blending process may involve a transition where spectral properties of a blend transition from an unsteady state (e.g., a heterogenous state at which properties of the blend vary with time) to a steady state (e.g., a homogenous state at which the properties of the blend remain substantially constant with time), with the steady state indicating that blending has been achieved. Therefore, accurate and reliable detection of the steady state based on spectral properties of the blend can both improve performance of the blending process (e.g., by ensuring adequate blending) and increase efficiency of the blending process (e.g., by enabling the blending process to be ended as soon as adequate blending has been achieved).

One conventional technique for detecting an end point of a blending process based on spectral properties is to use a moving F-test. According to this conventional technique, variance between two blocks of near-infrared (NIR) spectra collected during the blending process is evaluated to determine when a steady state, and therefore the end point of the blending process, has been reached. However, the conventional technique cannot provide robust end point detection and often detects the end point too early (i.e., the end point is detected before the blending process has actually reached the steady state). Other conventional techniques for detecting an end point of a blending process may use another type of moving block analysis, such as moving block standard deviation, moving block relative standard deviation, or moving block mean. However, these other types of moving block analysis rely on historical spectral data to set a threshold for detecting the steady state. Further, these other types of moving block analysis can also detect end points too early (e.g., similar to the moving F-test). As a result of these issues, the conventional techniques may be unreliable (e.g., due to early end point detection) and/or undesirably complex (e.g., due to a reliance on historical data).

Some implementations described herein include techniques and apparatuses that provide for improved detection of an end point of a dynamic process (e.g., a blending process). In some implementations, a device may receive spectroscopic data associated with the dynamic process. The device may identify a pseudo steady state end point based on the spectroscopic data, and may identify a reference block and a test block from the spectroscopic data based on the pseudo steady state end point. The device may generate a raw detection signal associated with the reference block and a raw detection signal associated with the test block, and then generate a statistical detection signal based on the raw detection signals. The device may then determine whether the dynamic process has reached a steady state based on the statistical detection signal. In some implementations, the techniques and apparatuses described herein provide for robust end point detection based on spectroscopic data collected during the dynamic process (e.g., without reliance on historical spectral data). Additional details are provided below.

Notably, while the implementations described herein are described in the context of a blending process, the implementations described herein can be applied to any type of dynamic process that moves from an unsteady state toward a steady state.

Figure 1B:
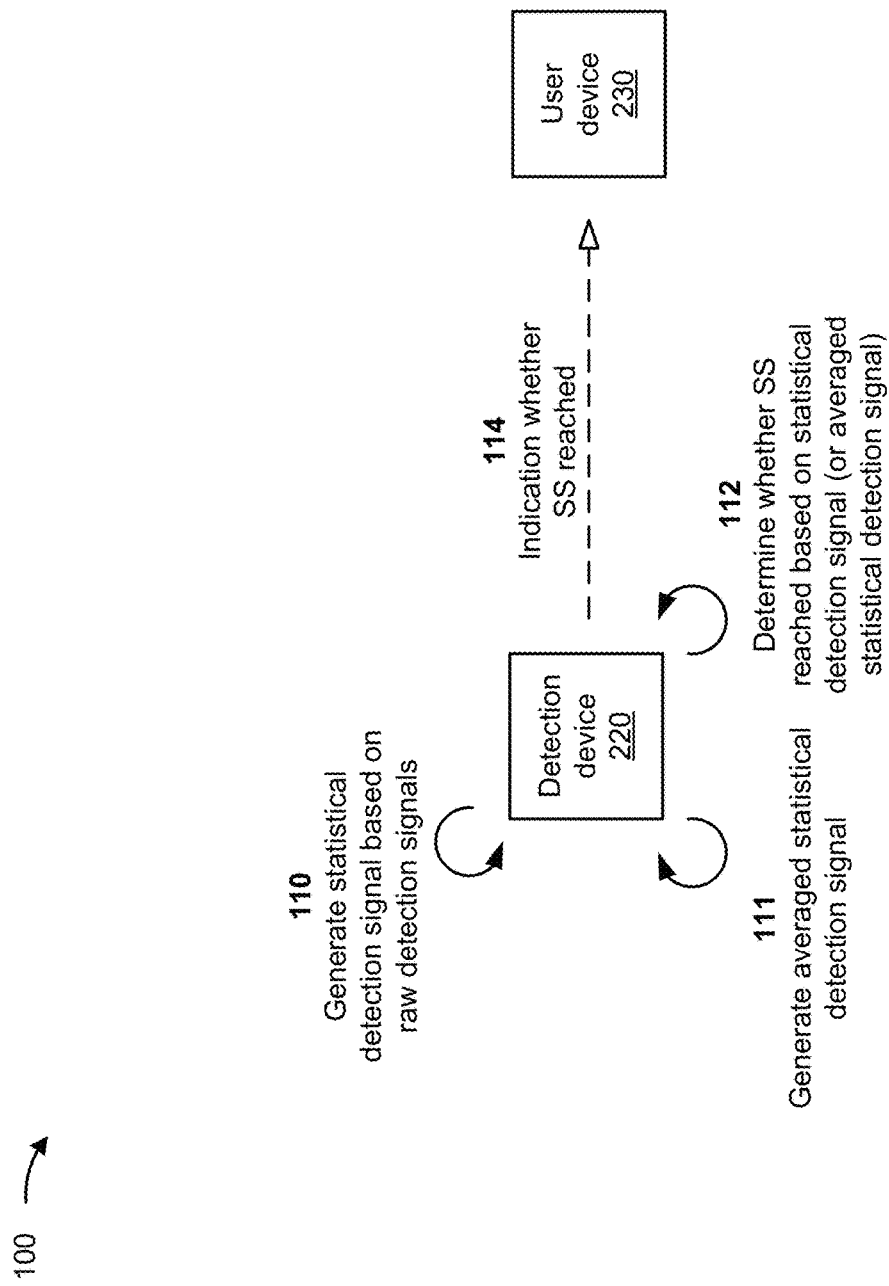
Figure 1C:
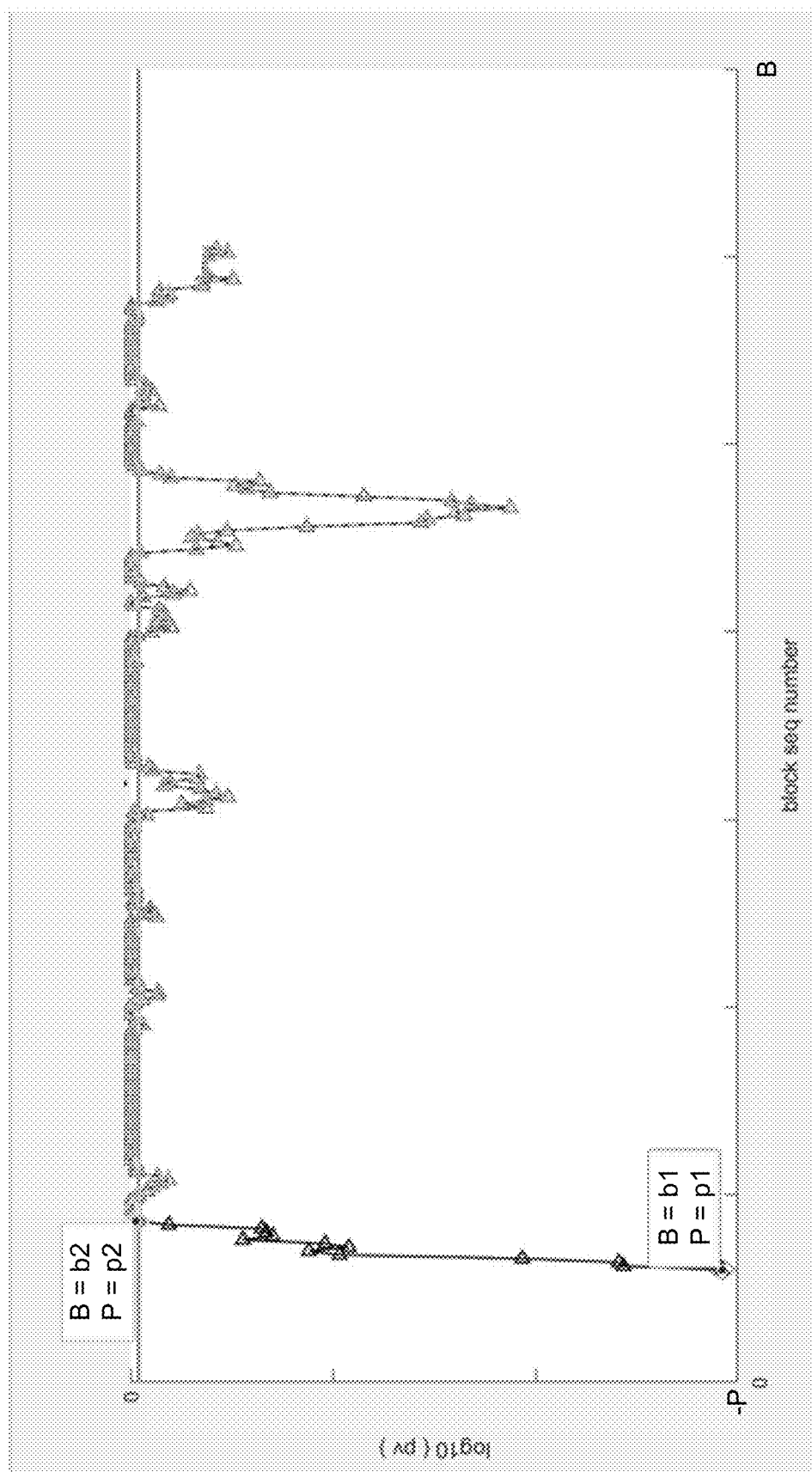
Figure 1D:
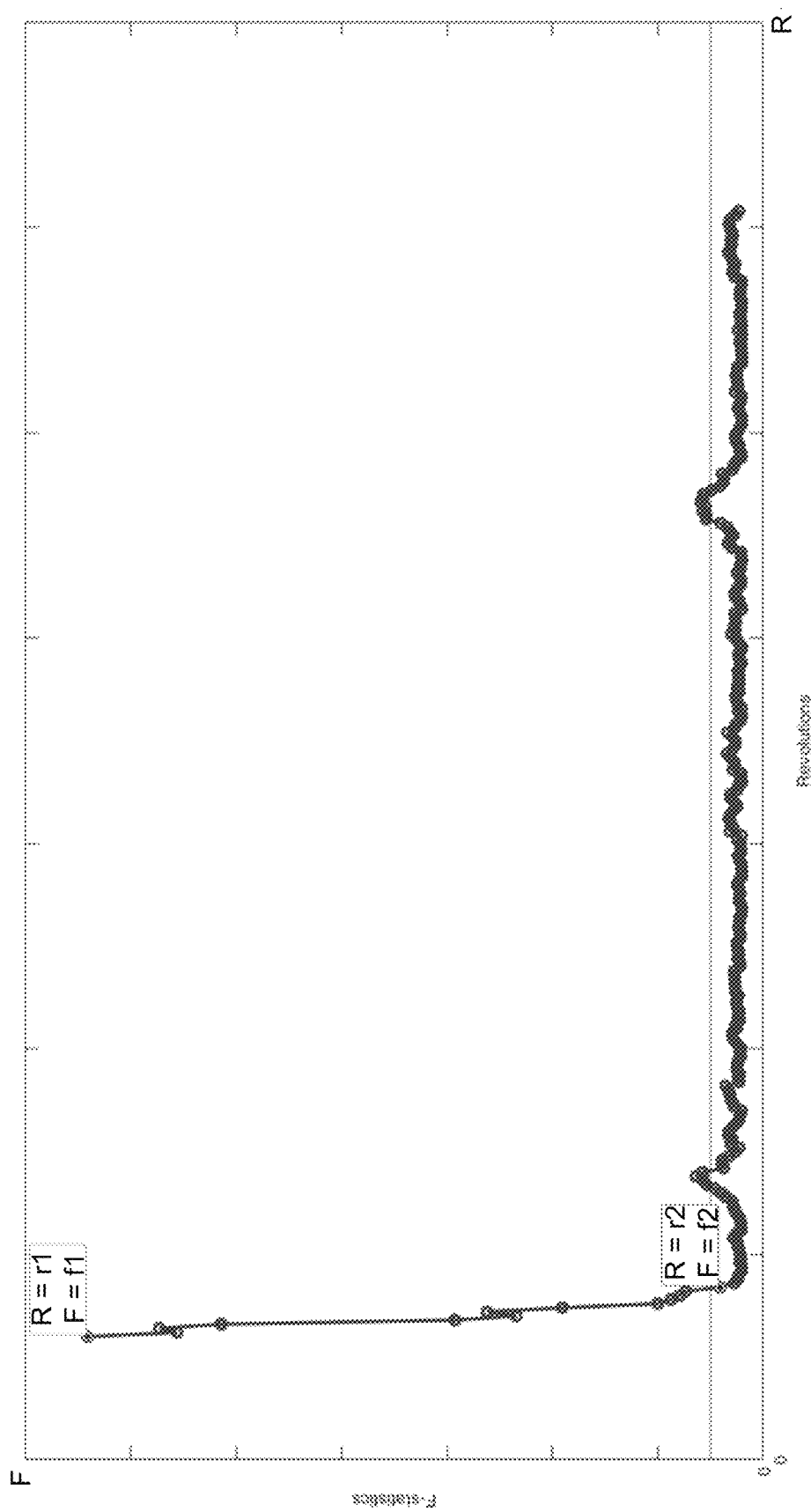
Figure 1E:
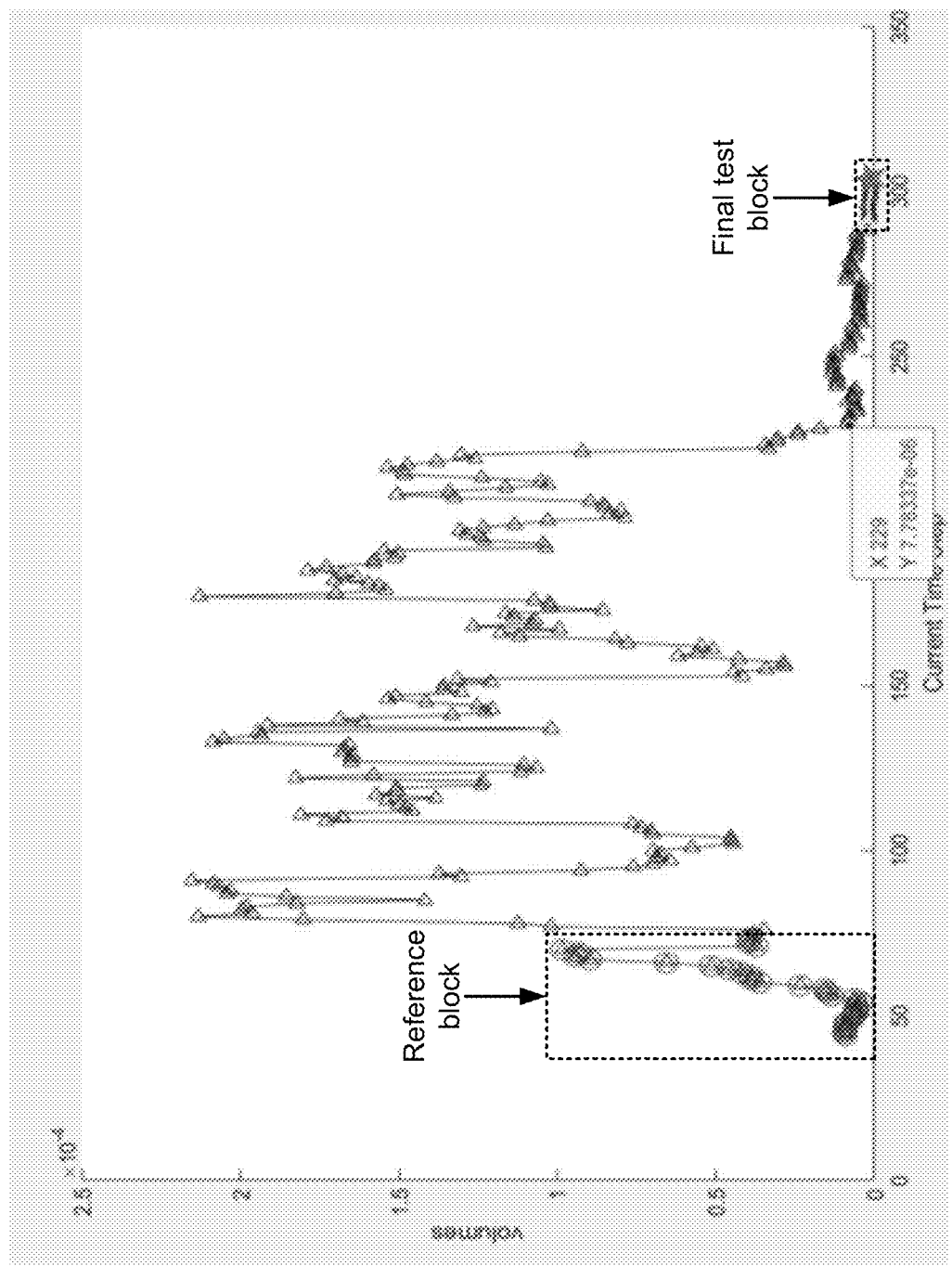
Figure 1F:
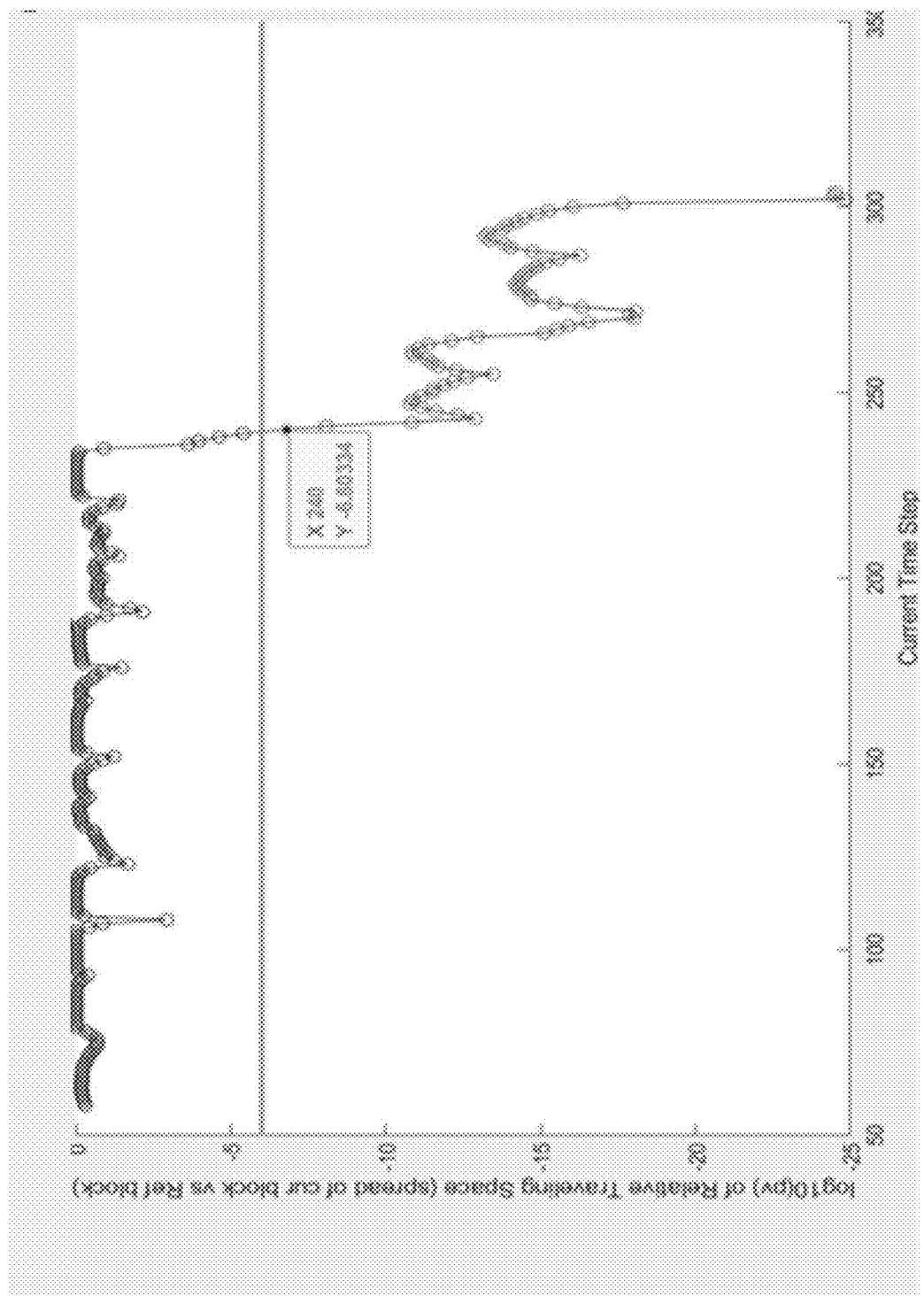
Figure 1G:
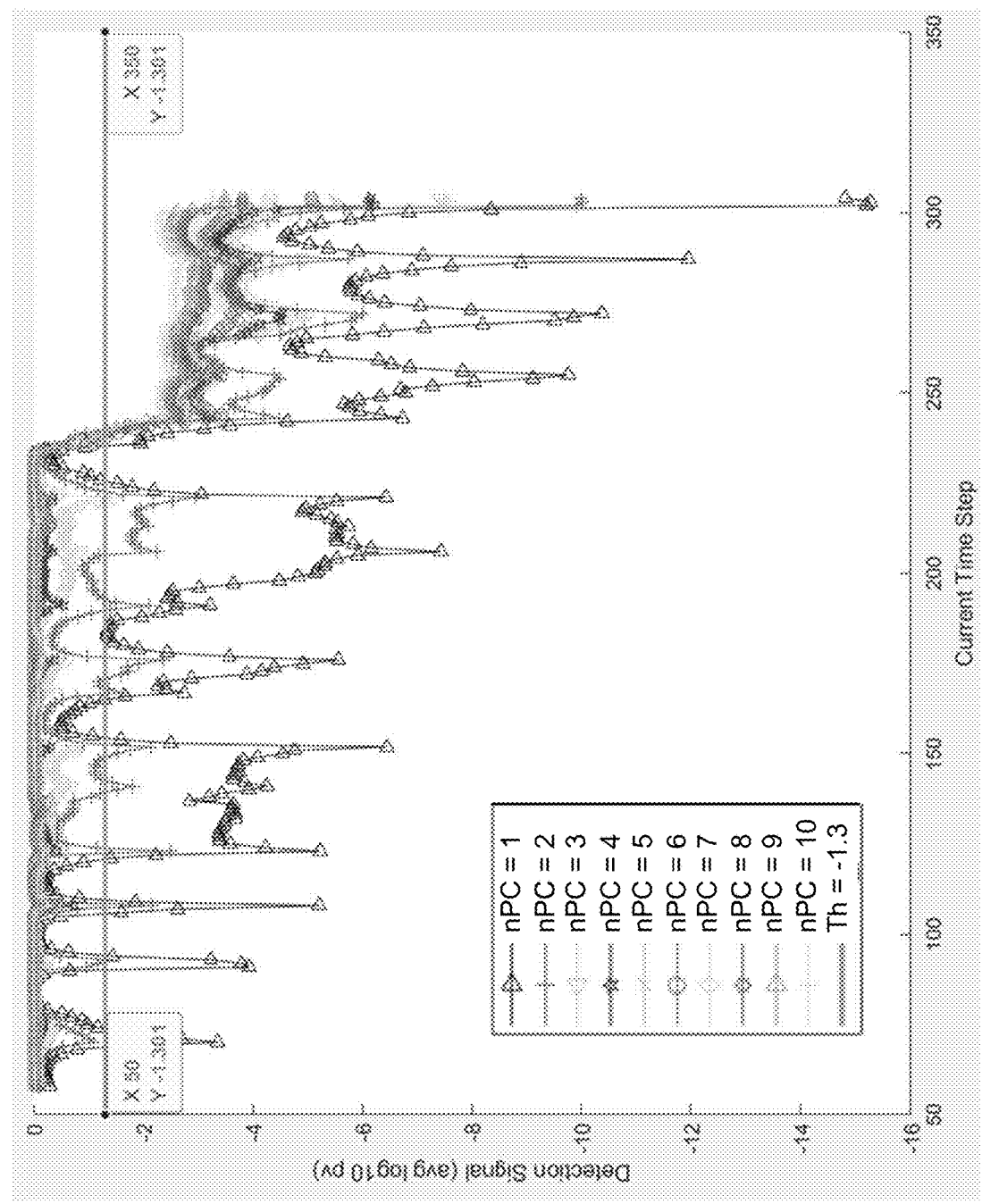
Figure 1H:
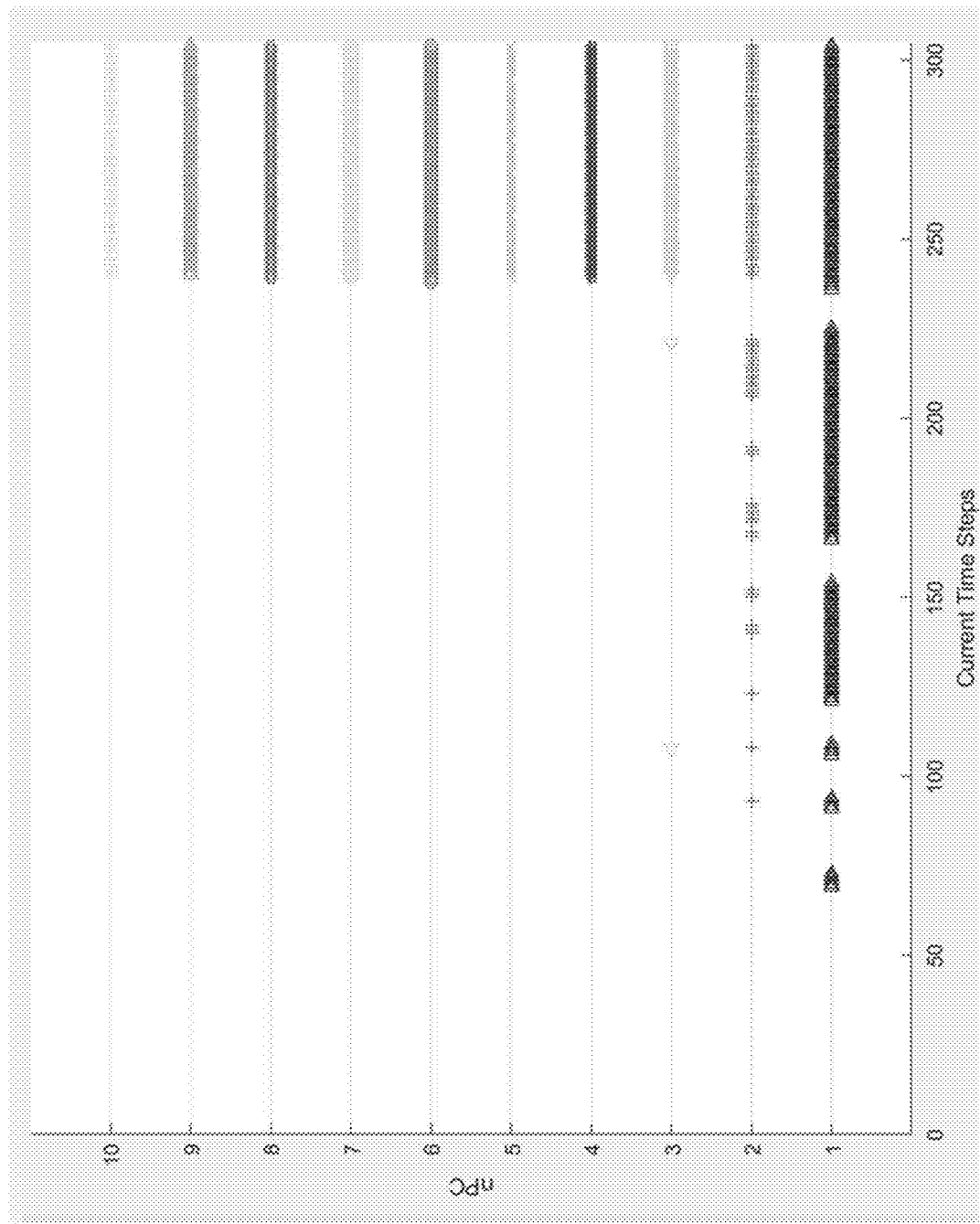
Figure 1I:
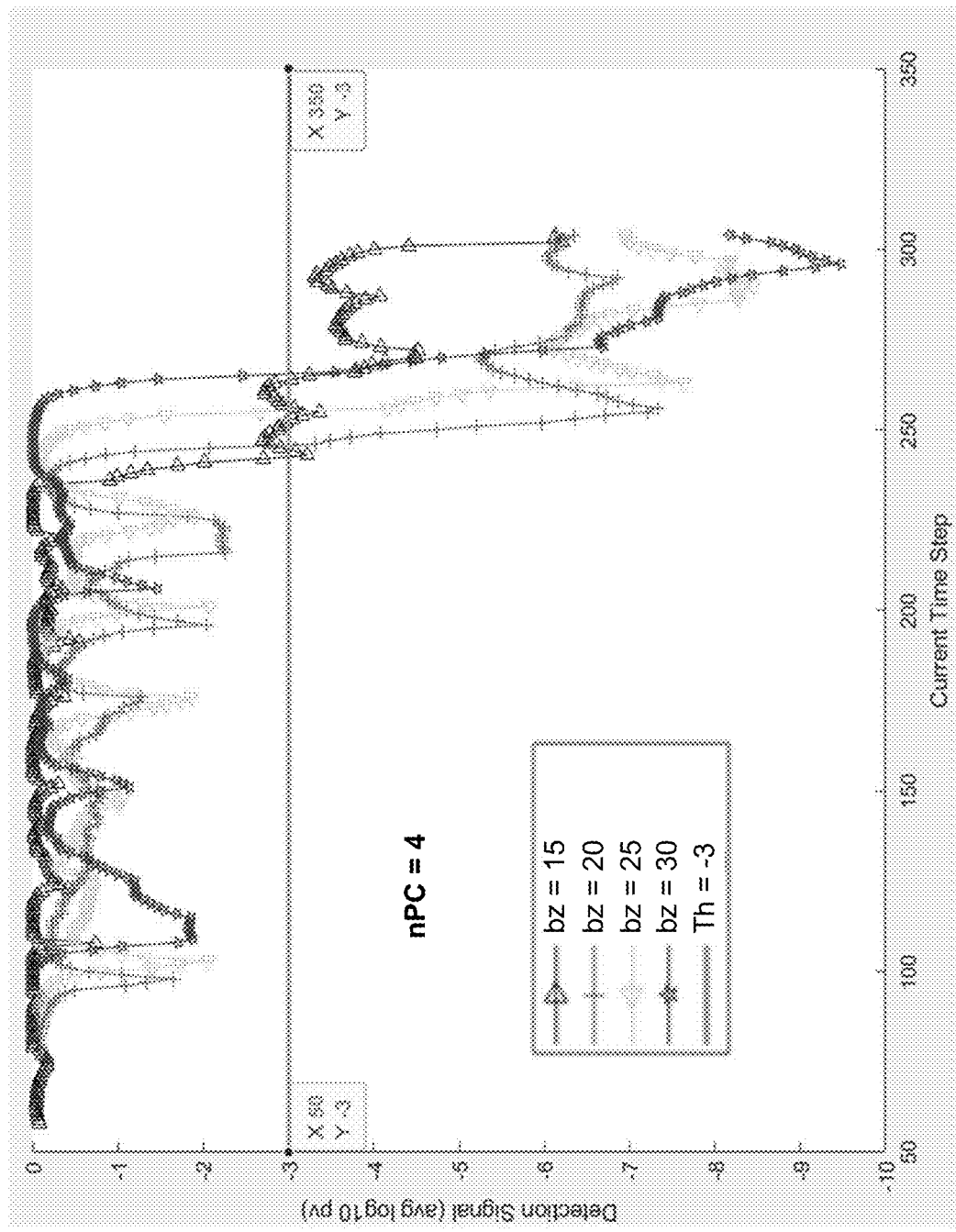
Figure 1J:
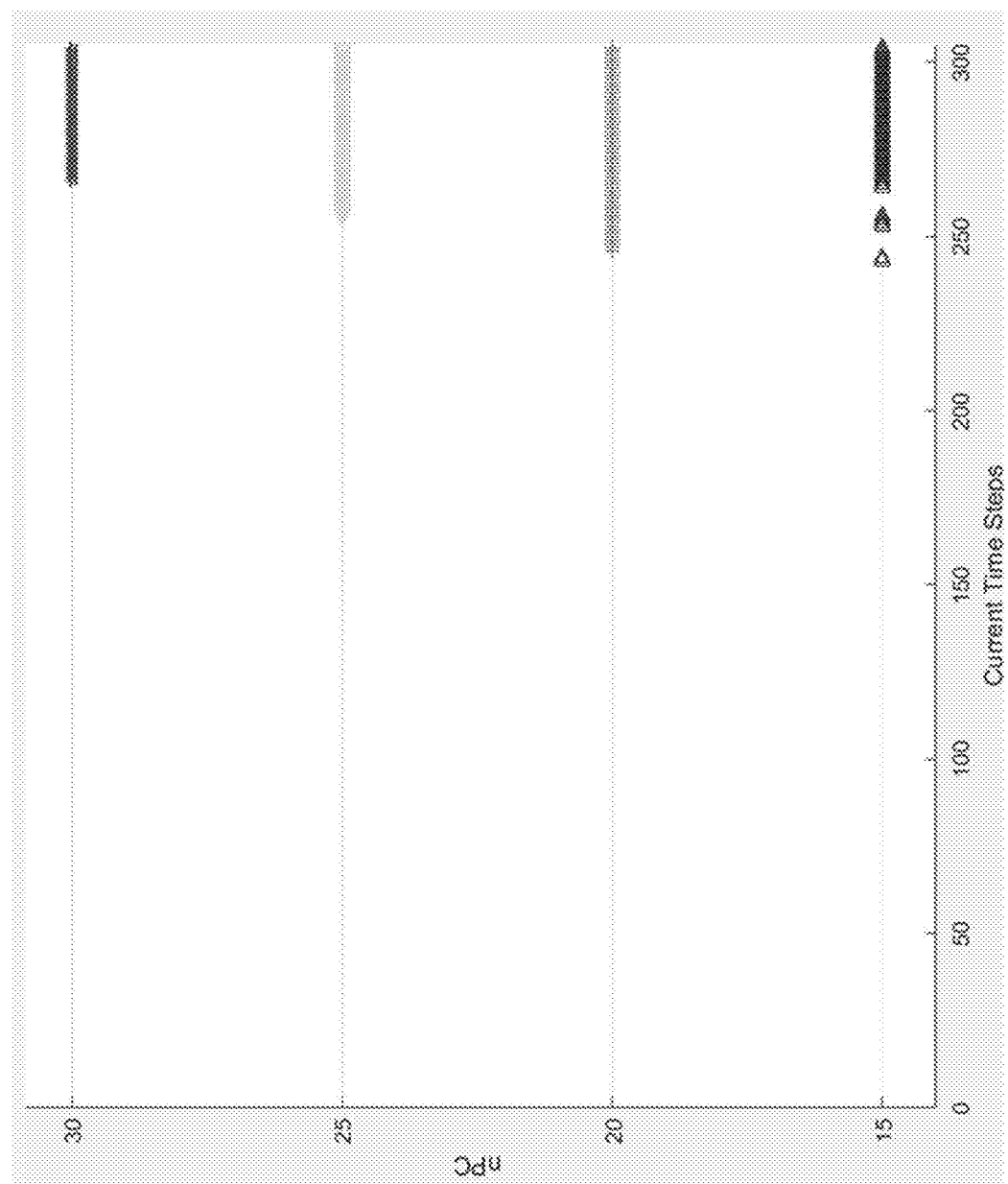
Figure 1K:
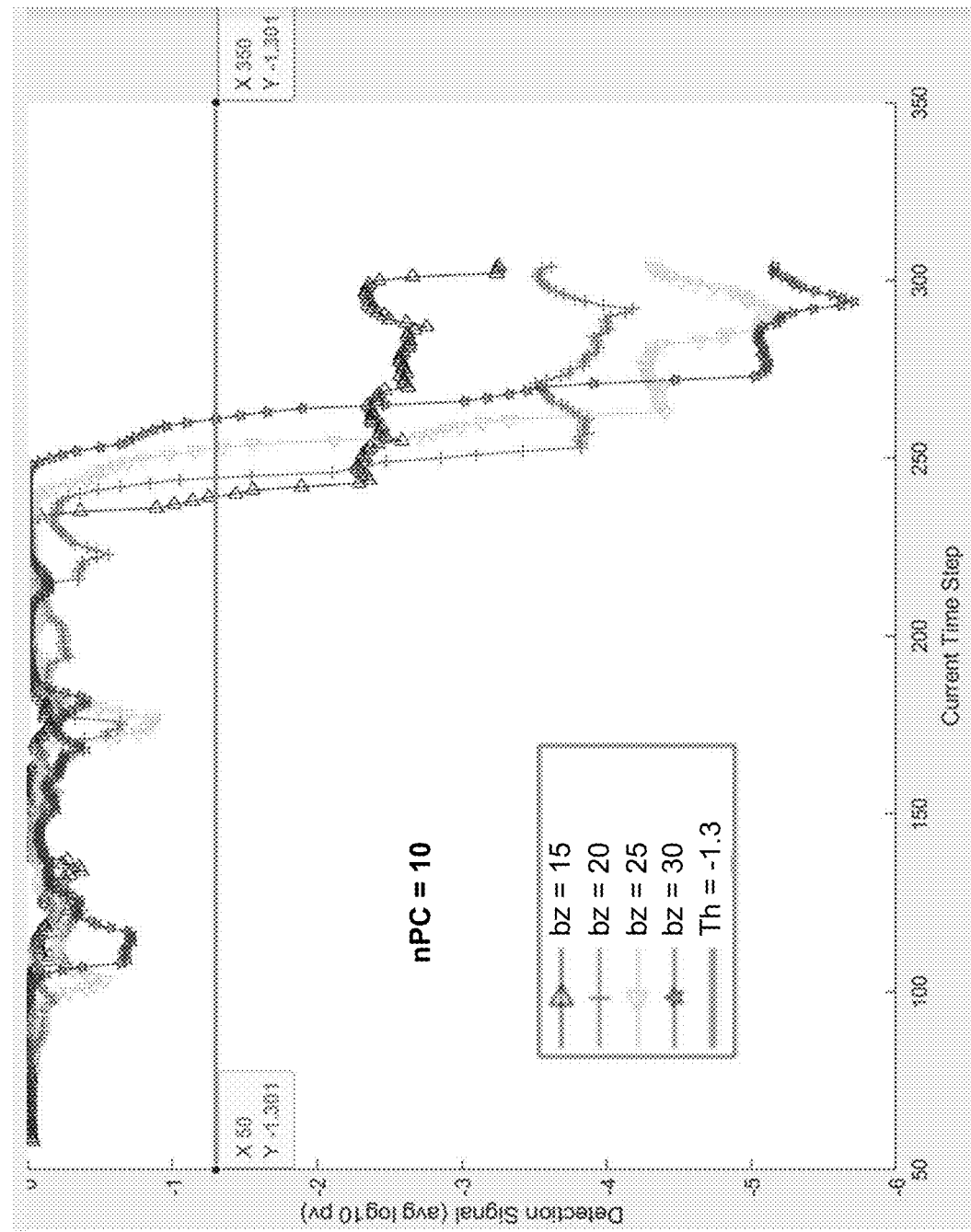
Figure 1L:
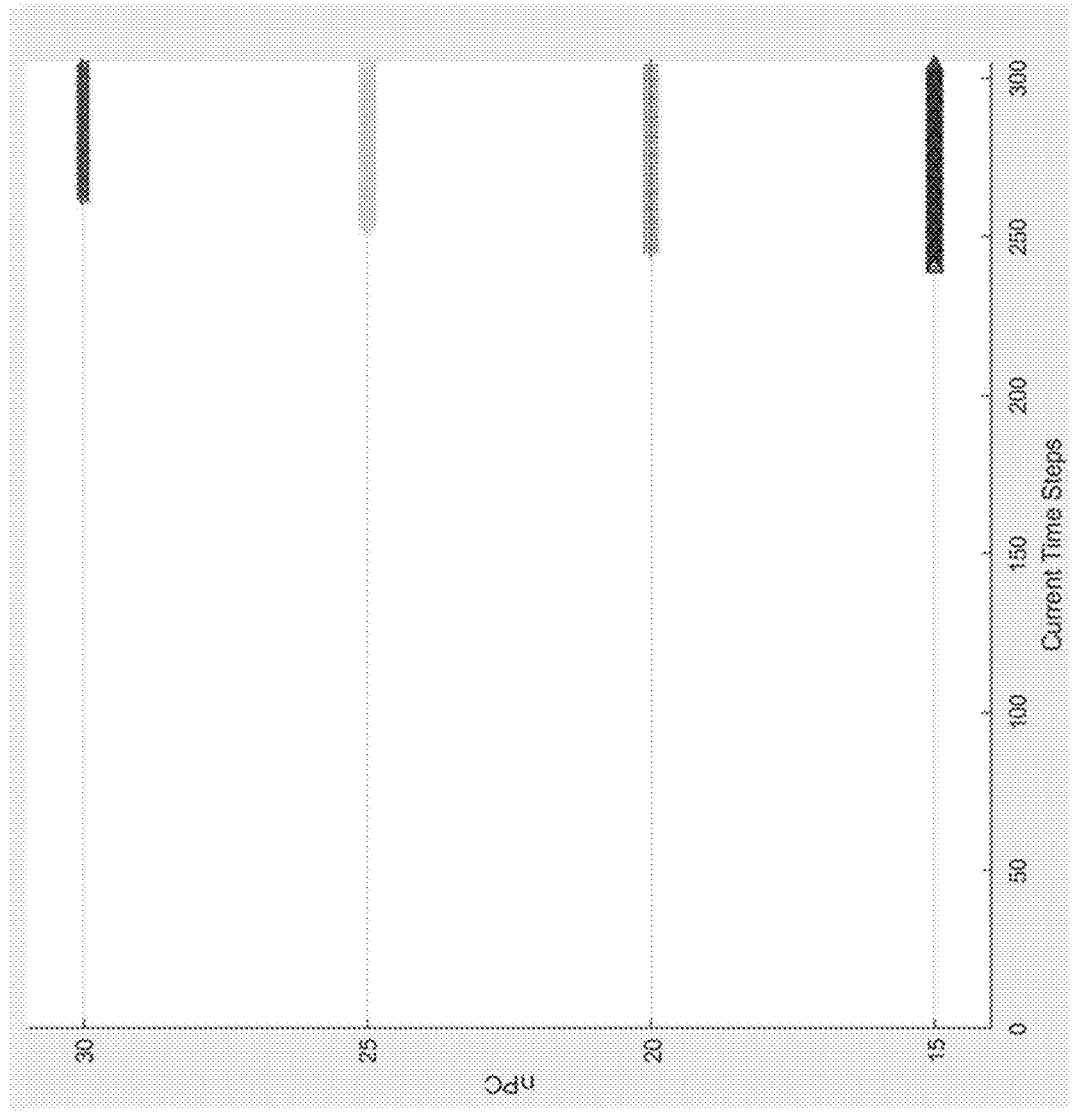
Figure 1M:
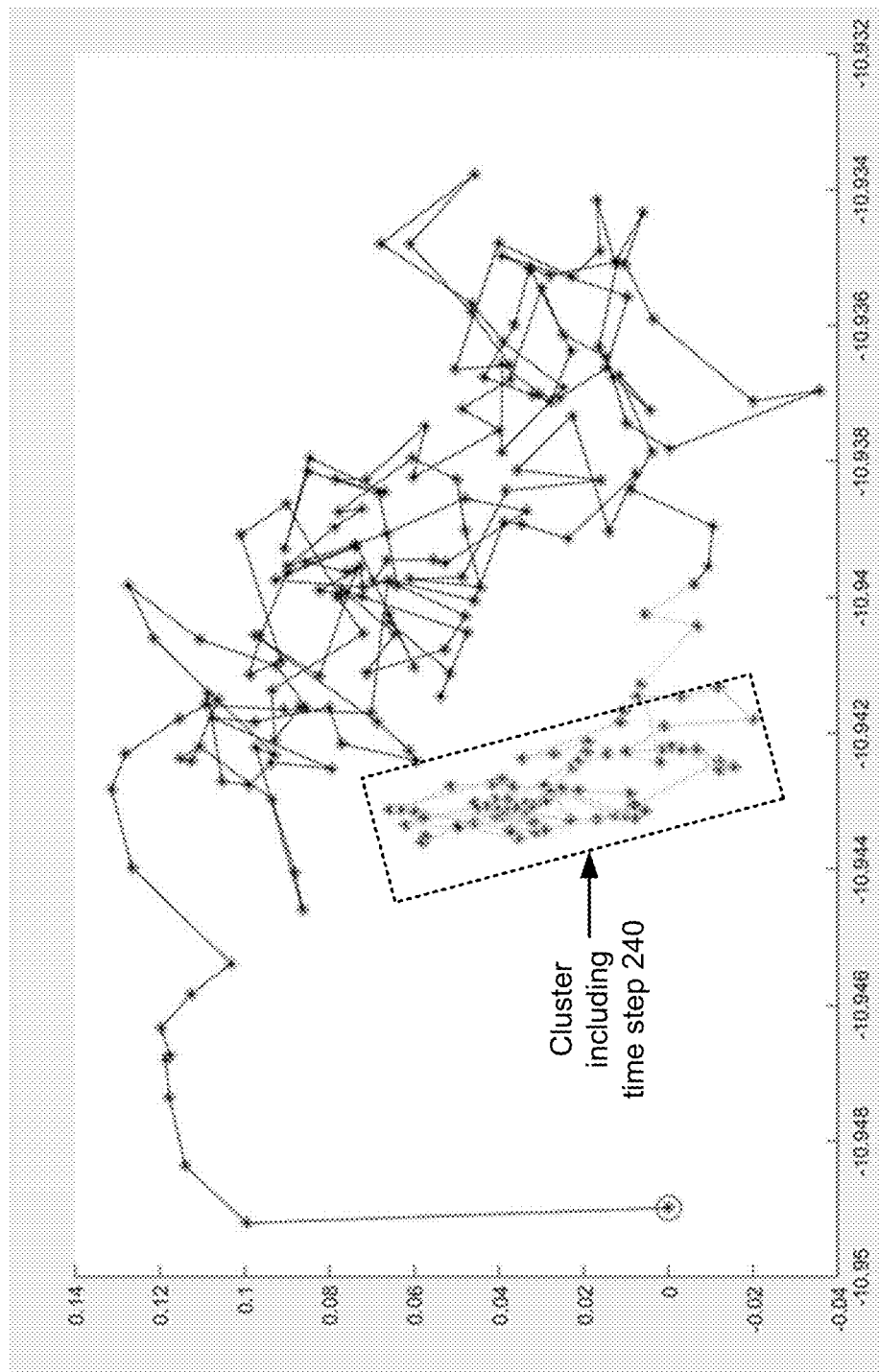
Figure 1N:
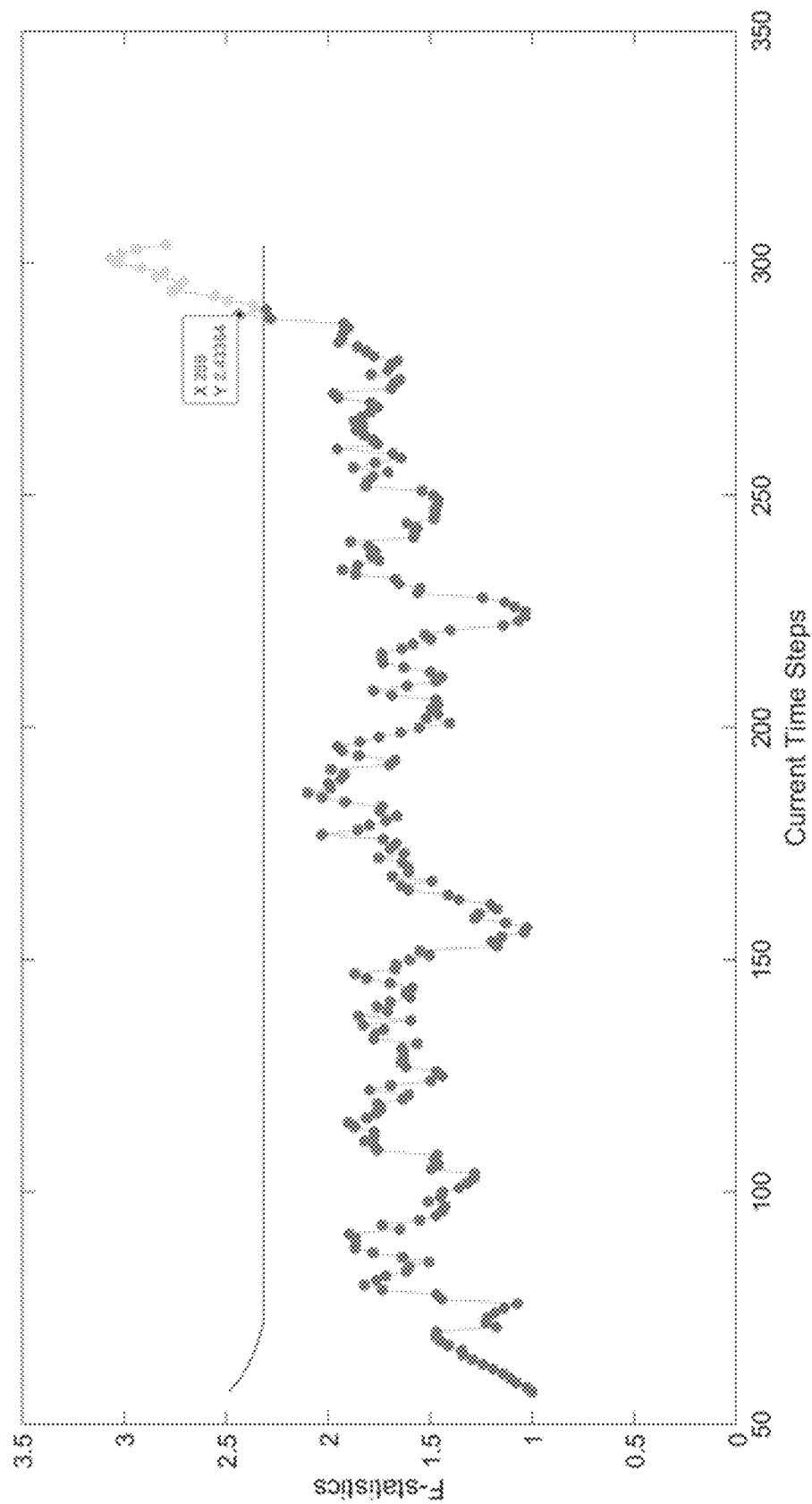

FIGS. 1A-1N are diagrams associated with blending process end point detection, as described herein. FIGS. 1A and 1B are diagrams illustrating an example implementation 100 of blending process end point detection. As shown in FIGS. 1A and 1B, the example implementation 100 includes a spectrometer 210, a detection device 220, and a user device 230.

As shown in FIG. 1A by reference 102, the detection device 220 may receive spectroscopic data associated with a blending process. For example, as shown, the spectrometer 210 may measure spectroscopic data at a given time during the performance of the blending process, and may provide the spectroscopic data to the detection device 220. In some implementations, the spectroscopic data includes spectra (e.g., multivariate time series data, such as NIR spectra) measured by the spectrometer 210 during a performance of the blending process.

In some implementations, the detection device 220 may receive the spectroscopic data in real-time or near real-time during the blending process. For example, detection device 220 may receive spectroscopic data, measured by the spectrometer 210 during the performance of the blending process, in real-time or near real-time relative to the spectrometer 210 obtaining the spectroscopic data during the blending process. In some implementations, the detection device 220 may determine, based on the spectroscopic data, whether an end point of the blending process has been reached, as described herein.

In some implementations, as shown by reference 104, the detection device 220 may identify a pseudo steady state end point based on the spectroscopic data. A pseudo steady state is a state of the blending process between an unsteady state and a steady state. Put another way, the pseudo steady state is a transition (or meta) state between the unsteady state and the steady state. While in the pseudo steady state, the blending process is neither in the unsteady state or the steady state. The pseudo steady state end point is a time point that indicates an end of the pseudo steady state. In some implementations, the detection device 220 identifies the pseudo steady state end point so that spectroscopic data corresponding to an unsteady state of the blending process can be ignored for the purpose of identifying the blending process end point, thereby reducing or eliminating noise resulting from the spectroscopic data corresponding to the unsteady state of the blending process and, in turn, improving reliability of blending process end point detection.

In some implementations, the detection device 220 may identify a junction point based on the pseudo steady state end point. The junction point is a time point at which the blending process transitions from the unsteady state to the pseudo steady state. That is, the junction point is a time point at which the pseudo steady state begins (e.g., a time point when the blending process enters the pseudo steady state). In some implementations, the detection device 220 may identify the junction point to enable visualization of the evolution of the blending process. For example, the detection device 220 may utilize the junction point to provide a visualization of the blending process that enables a user (e.g., a user of user device 230) to view an evolution history of the blending process (e.g., for monitoring the blending process in real-time or near real-time, for performing a post-run diagnosis of the blending process, for setting a parameter associated with the blending process, or the like).

In some implementations, in association with identifying the pseudo steady state end point (and the junction point), the detection device 220 may perform a rolling F-test of dual blocks of the spectroscopic data. For example, in some implementations, the detection device 220 may identify the pseudo steady state end point by calculating a first time point in the blending process at which a p-value (e.g., a probability of obtaining results at least as extreme as an observed result, under an assumption that a null hypothesis is correct) satisfies (e.g., is greater than or equal to) a p-value threshold. Therefore, in some implementations, the detection device 220 calculates p-values between moving dual blocks of the spectroscopic data such that the detection device 220 calculates p-values over time steps of the blending process. The detection device 220 then identifies the pseudo steady state end point as a time point (e.g., a first time point) at which the p-value satisfies the p-value threshold. In some implementations, the p-value threshold may be selectable or configurable by a user (e.g., to ensure that desired robustness is achieved). The p-value threshold may be, for example, 0.01, 0.02, 0.05, or another suitable value.

In some implementations, the detection device 220 may identify the junction point based on the spectroscopic data and the pseudo steady state end point. For example, in some implementations, when using p-values, the detection device 220 may identify the junction point by (1) identifying a time point when a minimum p-value occurs within a range of time steps (e.g., a range of time steps between a first time step of the blending process and the pseudo steady state end point), and (2) subtracting a block size (e.g., a size of the moving dual blocks expressed in time steps) from the identified time point.

FIG. 1C is a diagram illustrating an example associated with identification of a pseudo steady state end point and a junction point based on p-values calculated using a rolling F-test of dual blocks of spectroscopic data. In FIG. 1C, p-values (shown on the y-axis in log base 10) are calculated by the detection device 220 over time steps of the blending process (shown on the x-axis in terms of time points of ends of the moving dual blocks). As indicated in FIG. 1C, the moving dual blocks are initially significantly different from one another, which results in smaller p-values. However, as the blending process continues, the difference between the moving dual blocks decreases, meaning that the p-value increases over time. In the example shown in FIG. 1C, a first time step at which the p-value is greater than the p-value threshold is time step b2. Therefore, in this example, the detection device 220 identifies the pseudo steady state end point as time step b2. Notably, the conventional technique for end point detection described above would likely identify time step b2 as a time point at which the blending process is in the steady state. Additionally, in FIG. 1C, the minimum p-value is at time step b1 and the block size is half of that value, meaning that the junction point is identified as time step (b1)/2. In some implementations, the junction point is determined based on the minimum p-value since, at a junction between the moving dual blocks when the blending process transitions from the unsteady state to the pseudo steady state, one of the moving blocks is in the unsteady state and the other moving block is in the pseudo steady state and, therefore, the moving dual blocks should have the minimum p-value.

In some implementations, the detection device 220 may use F-values and an F-value threshold to identify the pseudo steady state end point and (optionally) the junction point (e.g., in addition to using p-values, or rather than using p-values). For example, in some implementations, the detection device 220 may identify the pseudo steady state end point by calculating a first time point in the blending process at which an F-value (e.g., a value calculated using an analysis to determine whether variances between two populations are significantly different) satisfies (e.g., is less than) an F-value threshold. Therefore, in some implementations, the detection device 220 calculates F-values between moving dual blocks such that the detection device 220 calculates F-values over time steps of the blending process, and identifies the pseudo steady state end point as the time point at which the F-value satisfies the F-value threshold. In some implementations, an F-value threshold used in association with identifying the pseudo steady state end point may be objectively generated (e.g., rather than being selected or configured by a user).

In some implementations, when using F-values, the detection device 220 may identify the junction point by (1) identifying a time point when a maximum F-value occurs within a range of time steps (e.g., a range of time steps between a first time step of the blending process and the pseudo steady state end point), and (2) subtracting a block size (e.g., a size of the moving dual blocks expressed in time steps) from the identified time point. In this example, the detection device 220 identifies the junction point by (1) identifying a time point when a maximum F-value occurs within a range of time steps (e.g., a range of time steps between a first time step of the blending process and the pseudo steady state end point), and (2) subtracting a block size from the identified time point.

FIG. 1D is a diagram illustrating an example associated with identification of a pseudo steady state end point based on a rolling F-test of dual-blocks of spectroscopic data using F-values. In FIG. 1D, F-values (shown on the y-axis) are calculated by the detection device 220 over time steps of the blending process (shown on the x-axis in terms of revolutions associated with the blending process). As indicated in FIG. 1D, the moving dual blocks are initially significantly different from one another, which results in larger F-values. However, as the blending process continues, the difference between the moving dual blocks decreases, meaning that the F-value decreases over time. In the example shown in FIG. 1D, a first time step at which the F-value is less than the F-value threshold is time step r2. Therefore, in this example, the detection device 220 identifies the pseudo steady state end point as time step r2. In FIG. 1D, the maximum F-value is at time step r1 and a block size is half that value, meaning that the junction point is identified as time step (r1)/2.

In some implementations, the detection device 220 may be configured to use both p-values and F-values by the detection device 220 in association with identifying the pseudo steady state end point and the junction point. In such a case, the detection device 220 may identify a first pseudo steady state end point and a first junction point using p-values and may identify a second pseudo steady state end point and a second junction point using F-values. Here, the detection device 220 may identify a pseudo steady state end point to be used for further data processing as a latest in time (e.g., most conservative) of the first and second pseudo steady state end points and, similarly, may identify a junction point to be used for further data processing as a latest in time of the first and second junction points. In this way, reliability and robustness of end point detection can be increased.

In some implementations, the detection device 220 may perform the rolling F-test, associated with identifying the pseudo steady state end point, on the whole spectrum of spectroscopic data within the moving dual blocks. For example, the detection device 220 may perform autoscaling or another type of pretreatment of the spectroscopic data within the moving dual blocks, and may perform the rolling F-test using the pretreated whole spectrum of spectroscopic data within the moving dual blocks. Notably, performing the rolling F-test on the whole spectrum may in some cases reduce complexity of computations performed by the detection device 220.

Additionally, or alternatively, the detection device 220 may perform the rolling F-test using a principal component analysis (PCA) model generated based on the spectroscopic data. For example, in some implementations, the detection device 220 may perform a PCA dimensional reduction on the spectroscopic data (e.g., a fixed set of spectra) to identify a set of principal components (e.g., two principal components, three principal components, four principal components, or the like) associated with the spectroscopic data. The detection device 220 may then generate a PCA model based on the identified principal components, and may calculate PCA scores using the PCA model. The detection device 220 may then perform the rolling F-test based on the PCA scores calculated using the PCA model.

Additionally, or alternatively, the detection device 220 may perform the rolling F-test using a PCA model generated based on historical spectroscopic data (e.g., spectroscopic data associated with a previously performed iteration of the blending process). For example, in some implementations, the detection device 220 may perform a PCA dimensional reduction on the historical spectroscopic data to identify a set of principal components (e.g., two principal components, three principal components, four principal components, or the like) associated with the historical spectroscopic data. The detection device 220 may then generate a historical PCA model based on the identified principal components. Here, the detection device 220 may use the historical model to calculate PCA scores associated with the moving dual blocks of the spectroscopic data. The detection device 220 may then perform the rolling F-test based on the PCA scores calculated using the historical PCA model. Notably, the use of historical spectroscopic data or a historical PCA model is not required, but can be used to increase reliability and robustness of end point detection. In some implementations, the detection device 220 may perform a PCA dimensional reduction on the spectroscopic data (i.e., the spectroscopic data associated with the current iteration of the blending process) or the historical spectroscopic data, and may then perform an F-test between a test block and a reference block of the spectroscopic data using a specific principal component (e.g., PC1, PC2, or the like). In some implementations, a moving F-test may be performed using the specific principal component. In this way, the analysis may be more chemistry specific since the specific principal component would correspond to specific chemical information.

Returning to FIG. 1A, as shown by reference 106, the detection device 220 may identify a reference block and a test block from the spectroscopic data based on the pseudo steady state end point. The reference block (also referred to as a reference individual block) is a block of spectral data starting at or near the pseudo steady state end point. For example, the reference block may include spectra for a particular quantity of time steps (e.g., 30 time steps) or block sizes (e.g., two block sizes) starting from a time point corresponding to the pseudo steady state end point. In some implementations, the reference block remains fixed (e.g., does not shift) as the detection device 220 receives additional spectroscopic data during the blending process.

The test block is a block of spectral data that can be compared to the reference block in association with determining whether the blending process has reached the steady state. In some implementations, the test block (also referred to as a test individual block) shifts dynamically based on newly received spectroscopic data. For example, a first test block may include spectra for a particular quantity of time steps (e.g., 15 time steps) or block sizes (e.g., one block size) starting from the time point corresponding to the pseudo steady state end point. In this example, a second test block (e.g., used for another iteration of generating a raw detection signal associated with the test block) may be updated to include spectra for the particular quantity of time steps (e.g., 15 time steps) or block sizes (e.g., one block size) starting from a time point corresponding to a time point that is after the time point corresponding to the pseudo steady state end point (e.g., an end point of the first test block, a mid-point of the first test block, a time point one or more steps later than the pseudo steady state end point, or the like). In this way, the test block can dynamically shift over time (e.g., as compared to the reference block, which may remain stationary). In some implementations, the stationary reference block and the dynamic test block form what is referred to as pseudo moving blocks (PMB) architecture.

As shown by reference 108, the detection device 220 may generate a raw detection signal associated with the reference block and a raw detection signal associated with the test block. The raw detection signal associated with the reference block and the raw detection signal associated with the test block are signals based on which the detection device 220 generates a statistical detection signal used to determine whether the blending process has reached an end point (e.g., whether the blending process is in the steady state).

In some implementations, the detection device 220 generates a raw detection signal (e.g., the raw detection signal associated with the reference block and/or the raw detection signal associated with the test block) by calculating a travel space volume (TSV) associated with a block (e.g., the reference block or the test block) of spectroscopic data. A TSV is a hyper-dimensional volume swept by multivariate time series spectral data within a time frame corresponding to the block, where a quantity of time steps covered by the block defines a block size. Therefore, a TSV for the reference block may be a hyper-dimensional volume swept by spectroscopic data corresponding to the reference block (e.g., spectra for 30 time steps from the end of the pseudo steady state), and a TSV for the test block may be a hyper-dimensional volume swept by spectroscopic data corresponding to the test block (e.g., spectra for 15 time steps of the moving test block). In some implementations, the detection device 220 may calculate a TSV by calculating a volume of a convex hull of swept space within a block. Additionally, or alternatively, the detection device 220 may calculate a TSV by calculating a volume of a hyper-dimensional ellipsoid (e.g., a multivariate confidence ellipsoid based on Hotelling's T2 distribution). Additionally, or alternatively, the detection device 220 may calculate a TSV by calculating a product of a standard deviation of each principal component of spectroscopic data corresponding to a block (e.g., when the detection device 220 is configured to perform PCA dimensional reduction). Additionally, or alternatively, the detection device 220 may calculate a TSV by calculating a product of a standard deviation of each wavelength of the spectroscopic data corresponding to the block (e.g., when the detection device 220 is configured to use the whole spectrum of the spectroscopic data).

Additionally, or alternatively, the detection device 220 generates a raw detection signal (e.g., the raw detection signal associated with the reference block and/or the raw detection signal associated with the test block) by calculating an individual block standard deviation (IBSD) associated with a block (e.g., the reference block or the test block) of spectroscopic data. Therefore, an IBSD for the reference block may be an IBSD associated with spectroscopic data corresponding to the reference block, and an IBSD for the test block may be an IBSD associated with spectroscopic data corresponding to the test block. In some implementations, the detection device 220 may calculate an IBSD by calculating a sum of squares of standard deviations of each principal component of spectroscopic data corresponding to a block (e.g., when the detection device 220 is configured to perform PCA dimensional reduction). Additionally, or alternatively, the detection device 220 may calculate an IBSD by calculating a sum of squares of standard deviations of each wavelength of the spectroscopic data corresponding to the block (e.g., when the detection device 220 is configured to use the whole spectrum of the spectroscopic data).

As shown in FIG. 1B by reference 110, the detection device 220 may generate a statistical detection signal based on the raw detection signal associated with the reference block and the raw detection signal associated with the test block. The statistical detection signal is a signal based on which the detection device 220 can determine whether the blending process has reached the steady state.

In some implementations, in association with generating the statistical detection signal, the detection device 220 may perform a rolling F-test between the reference block and the test block using the raw detection signal associated with the reference block and the raw detection signal associated with the test block. For example, in some implementations, the detection device 220 calculates p-values between the reference block and the test block such that the detection device 220 calculates p-values throughout the blending process. Here, the statistical detection signal is represented by the p-values calculated by the detection device 220 throughout the blending process. As another example, in some implementations, the detection device 220 calculates F-values between the reference block and the test block such that the detection device 220 calculates F-values throughout the blending process. Here, the statistical detection signal is represented by the F-values calculated by the detection device 220 throughout the blending process. In some implementations, the statistical detection signal (e.g., rather than a raw detection signal) is used to improve robustness of the end point detection process.

In some implementations, as shown by reference 111, the detection device 220 may generate an averaged statistical detection signal. In some implementations, the detection device 220 may generate the averaged statistical detection signal based on the statistical detection signal. For example, to generate the averaged statistical detection signal, the detection device 220 may in some implementations generate the statistical detection signal (e.g., in the manner described above), and then average the statistical detection signal based on a number of principal components associated with the statistical detection signal. That is, the detection device 220 may divide the statistical detection signal by a number of principal components (e.g., a number of principal components associated with a PCA performed on the spectroscopic data), where a result of the division is the averaged statistical detection signal. In some implementations, the number of principal components (nPC) may be greater than or equal to one (nPC≥1), such as four or more (e.g., nPC=4, nPC=10, or the like). Additionally, or alternatively, the detection device 220 may in some implementations generate the averaged statistical detection signal based on the raw detection signal associated with the reference block and the raw detection signal associated with the test block. That is, in some implementations, the detection device 220 may generate the averaged statistical detection signal without separately generating the statistical detection signal (e.g., the detection device 220 may generate the statistical detection signal as a sub-step of generating the averaged statistical detection signal).

In some implementations, the averaged statistical detection signal is an averaged p-value signal. For example, the statistical detection signal may be a p-value signal, and dividing the p-value signal by the number of principal components provides the averaged statistical detection signal in the form of an averaged p-value signal. Thus, in some implementations, the steady state threshold used to determine whether the blending process has reached a steady state (e.g., as described below with respect to reference 112) is a p-value threshold. In some implementations, the p-value threshold applied when the detection device 220 uses the averaged statistical detection signal to determine whether the blending process has reached the steady state may be a value that is greater than or equal to approximately 0.01, such as 0.05.

As shown by reference 112, the detection device 220 may determine whether the blending process has reached a steady state based on the statistical detection signal or the averaged statistical detection signal. For example, the detection device 220 may determine whether the statistical detection signal (e.g., the p-value, the F-value, or the like) satisfies a condition associated with a steady state threshold. As a particular example, if the statistical detection signal is a p-value signal, then the detection device 220 may determine whether the value of the statistical detection signal is less than or equal to a p-value steady state threshold. Here, if detection device 220 determines that the value of the statistical detection signal is greater than the p-value steady state threshold, then the detection device 220 may determine that the blending process has not reached the steady state. Conversely, if detection device 220 determines that the value of the statistical detection signal is less than or equal to the p-value steady state threshold, then the detection device 220 may determine that the blending process has reached the steady state. As another example, if the averaged statistical detection signal is a p-value signal, then the detection device 220 may determine whether the value of the averaged statistical detection signal is less than or equal to a p-value steady state threshold. Here, if detection device 220 determines that the value of the averaged statistical detection signal is greater than the p-value steady state threshold, then the detection device 220 may determine that the blending process has not reached the steady state. Conversely, if detection device 220 determines that the value of the averaged statistical detection signal is less than or equal to the p-value steady state threshold, then the detection device 220 may determine that the blending process has reached the steady state. As another example, if the statistical detection signal is an F-value signal, the detection device 220 may determine whether the value of the statistical detection signal is greater than or equal to an F-value steady state threshold. Here, if detection device 220 determines that the value of the statistical detection signal is less than the F-value steady state threshold, then the detection device 220 may determine that the blending process has not reached the steady state. Conversely, if detection device 220 determines that the value of the statistical detection signal is greater than or equal to the F-value steady state threshold, then the detection device 220 may determine that the blending process has reached the steady state. As another example, if the averaged statistical detection signal is an F-value signal, the detection device 220 may determine whether the value of the averaged statistical detection signal is greater than or equal to an F-value steady state threshold. Here, if detection device 220 determines that the value of the averaged statistical detection signal is less than the F-value steady state threshold, then the detection device 220 may determine that the blending process has not reached the steady state. Conversely, if detection device 220 determines that the value of the averaged statistical detection signal is greater than or equal to the F-value steady state threshold, then the detection device 220 may determine that the blending process has reached the steady state.

In some implementations, the condition associated with the steady state threshold may require a particular quantity of consecutive values of the statistical detection signal or the averaged statistical detection signal to satisfy the steady state threshold (e.g., to improve robustness and reliability of the end point detection). For example, the condition may require that seven consecutive values of the statistical detection signal or the averaged statistical detection signal satisfy the steady state threshold (e.g., that seven consecutive p-values be less than or equal to the p-value steady state threshold, that seven consecutive F-values be greater than or equal to the F-value steady state threshold, that six consecutive p-values be less than or equal to the p-value steady state threshold, that six consecutive F-values be greater than or equal to the F-value steady state threshold, or the like). In some implementations, the quantity of consecutive values required may be selected based on a binomial probability function (e.g., to sufficiently reduce a likelihood of a false positive end point detection). In some implementations, the steady state threshold may be selectable or configurable by a user (e.g., when the statistical detection signal or the averaged statistical detection signal is a p-value signal). Alternatively, in some implementations, the steady state threshold may be objectively computed by the detection device 220 (e.g., when the statistical detection signal or the averaged statistical detection signal is an F-value signal or when the averaged statistical detection signal is a p-value signal).

As shown by reference 114, the detection device 220 may (optionally) provide an indication of whether the steady state has been reached. For example, the detection device 220 may provide, to a user device 230, an indication of whether the blending process has reached the steady state. As a particular example, if the detection device 220 has determined that the blending process has reached the steady state, then the detection device 220 may provide, to a user device 230 associated with monitoring or controlling the blending process, an indication that the blending process has reached the steady state. As another particular example, if the detection device 220 determines that the blending process has not reached the steady state, then the detection device 220 may provide, to the user device 230, an indication that the blending process has not reached the steady state. In this way, a user of the user device 230 can be informed of whether the blending process has reached the steady state (e.g., such that the user can monitor or adjust the blending process, as needed).

As another example, the detection device 220 may provide the indication of whether the blending process has reached the steady state in order to cause an action to be automatically performed. For example, if the detection device 220 determines that the blending process is in the steady state, then the detection device 220 may provide an indication to one or more other devices, such as a device associated with performing the blending process (e.g., to cause the device to stop the blending process, to cause the blending process to be restarted on new raw materials, or the like) or a device associated with performing a next step of the manufacturing process (e.g., to cause the next step in the manufacturing process to be initiated), among other examples.

In some implementations, the detection device 220 may provide the junction point and/or information associated with the junction point to the user device 230 to, for example, enable visualization of the evolution of the blending process via the user device 230.

FIGS. 1E-1M are diagrams illustrating example results associated with blending process end point detection performed as described above with respect to example implementation 100. FIGS. 1E-1M are diagrams illustrating results when a detection device 220 is configured to utilize p-values for blending process end point detection.

FIG. 1E illustrates TSVs calculated by the detection device 220 throughout an iteration of the blending process. In the example shown in FIG. 1E, TSVs are computed as a product of a standard deviation of each of four principal components identified from the spectroscopic data using a PCA dimensional reduction. The test block moves as the detection device 220 receives spectroscopic data throughout the blending process. A final test block is indicated on the right hand side of the figure.

FIG. 1F is a diagram illustrating a statistical detection signal generated based on the TSVs associated with FIG. 1E. In FIG. 1F, the y-axis shows p-values (in log base 10) and a steady state threshold is set at −6. In this example, the detection device 220 determines that the p-value first satisfies the steady state threshold at time step 240, meaning that the detection device 220 may determine that the end point of the blending process is at (or shortly after) time step 240. Notably, using the same set of spectroscopic data, the conventional technique would identify the end point of the blending process at time step 42 (e.g., at approximately the end point of the pseudo steady state).

FIGS. 1G and 1H are diagrams illustrating an averaged statistical detection signal associated with blending process end point detection performed as described above with respect to example implementation 100.

As described above, the detection device 220 may in some implementations generate an averaged statistical detection signal for use in association with determining whether the blending process has reached the steady state. For example, the detection device 220 may average logarithmic p-values (e.g., in log base 10) of the statistical detection signal, with an average of the logarithmic p-values being determined based on dividing a logarithmic p-value by a number of principal components nPC (e.g., averaged logarithmic p-value=$\log_{10}$(p-value)/nPC). As one example, for four principal components, an averaged logarithmic p-value may be determined as $\log_{10}$(p-value)/4. FIG. 1G illustrates examples of averaged logarithmic p-values (i.e., averaged statistical detection signals) generated from a set of spectroscopic data for different numbers of principal components (e.g., nPC=1 through nPC=10). As described above, the detection device 220 may then determine whether an averaged p-value satisfies a steady state threshold (e.g., a p-value threshold) in order to determine whether the blending process has reached the steady state.

In some implementations, the use of an averaged statistical detection signal enables a less aggressive steady state threshold to be used for determination of whether the blending process has reached the steady state (e.g., as compared to a threshold used when using an unaveraged statistical detection signal). For example, with reference to FIGS. 1G and 1H, a steady state threshold of p-value=0.05 (Th=$\log_{10}$(0.05)=−1.3) is used. As shown, for four through ten dimensions of principal components, a steady state threshold of −1.3 provides satisfactory information regarding the end point of the blending process. This may mean that numbers of principal components from four to ten are acceptable for determination of whether the blending process has reached the steady state. Conversely, if an unaveraged statistical detection signal (e.g., an unaveraged logarithm of a p-value) is used, then the steady state threshold may need to be comparatively more aggressive (e.g., a comparatively smaller p-value) to reliably detect whether the blending process has reached the steady state.

FIGS. 1I-1L are diagrams illustrating an effect of block size on an averaged statistical detection signal associated with blending process end point detection performed as described above with respect to example implementation 100. In some implementations, using the averaged statistical detection signal (e.g., an averaged $\log_{10}$ p-value) may provide reliable detection of whether the blending process has reached the steady state for a larger range of block sizes (e.g., as compared to a range of block sizes when using the unaveraged statistical detection signal).

For example, FIGS. 1I and 1J illustrate an impact of different block sizes (bz) on an averaged statistical detection signal associated with four principal components. A steady state threshold of p-value=0.001 (Th=$\log_{10}$(0.001)=−3) is used in the example shown in FIGS. 1I and 1J. As illustrated by FIGS. 1I and 1J, the steady state threshold is satisfactory to determine whether the blending process has reached the steady state across all block sizes for the averaged statistical detection signal associated with four principal components.

As another example, FIGS. 1K and 1L illustrate an impact of different block sizes on an averaged statistical detection signal associated with ten principal components. A steady state threshold of p-value=0.05 (Th=$\log_{10}$(0.05)=−1.3) is used in the example shown in FIGS. 1K and 1L. As illustrated by FIGS. 1K and 1L, the steady state threshold is satisfactory to determine whether the blending process has reached the steady state across all block sizes for the averaged statistical detection signal associated with ten principal components.

FIG. 1M is a diagram illustrating PCA trajectories that further convey the capability of the detection device 220 to detect the end point of the blending process. As illustrated in FIG. 1M, data points corresponding to spectroscopic data for a time period after the end point determined by the detection device 220 as illustrated in FIG. 1F (i.e., spectroscopic data after time step 240) progress into a comparatively tighter cluster, which indicates that a steady state of blending (i.e., blend homogeneity) has been achieved.

FIG. 1N is a diagram illustrating blending process end point detection performed using F-values based on IBSD, as described above. As noted above, larger F-values (or smaller p-values) indicate that the test block is relatively more different from the reference block, which explains a downward trend of the blending profile in FIG. 1F and an upward trend of the blending profile in FIG. 1N. In the example shown in FIG. 1N, the end point should be above the determined F-value threshold. In this example, the end point of the blending process is determined to be time step 289, which implies that the tightest cluster of points of spectral data shown in FIG. 1M has reached the steady state. Notably, from a practical perspective, there is no significant difference between stopping the blending process at the time step 240 or time step 289 in this example (e.g., a 3 minute difference). However, importantly, detection device 220 would not have stopped the blending process unreasonably early (as would have occurred if the conventional technique were employed). In some implementations, as described above, the detection device 220 may be configured to use p-values and F-values in association with determining the end point of the blending process, in which case a more conservative (e.g., later) end point identified by the detection device 220 may be used.

As indicated above, FIGS. 1A-1N are provided as examples. Other examples are possible and may differ from what was described with regard to FIGS. 1A-1N.

Figure 2:
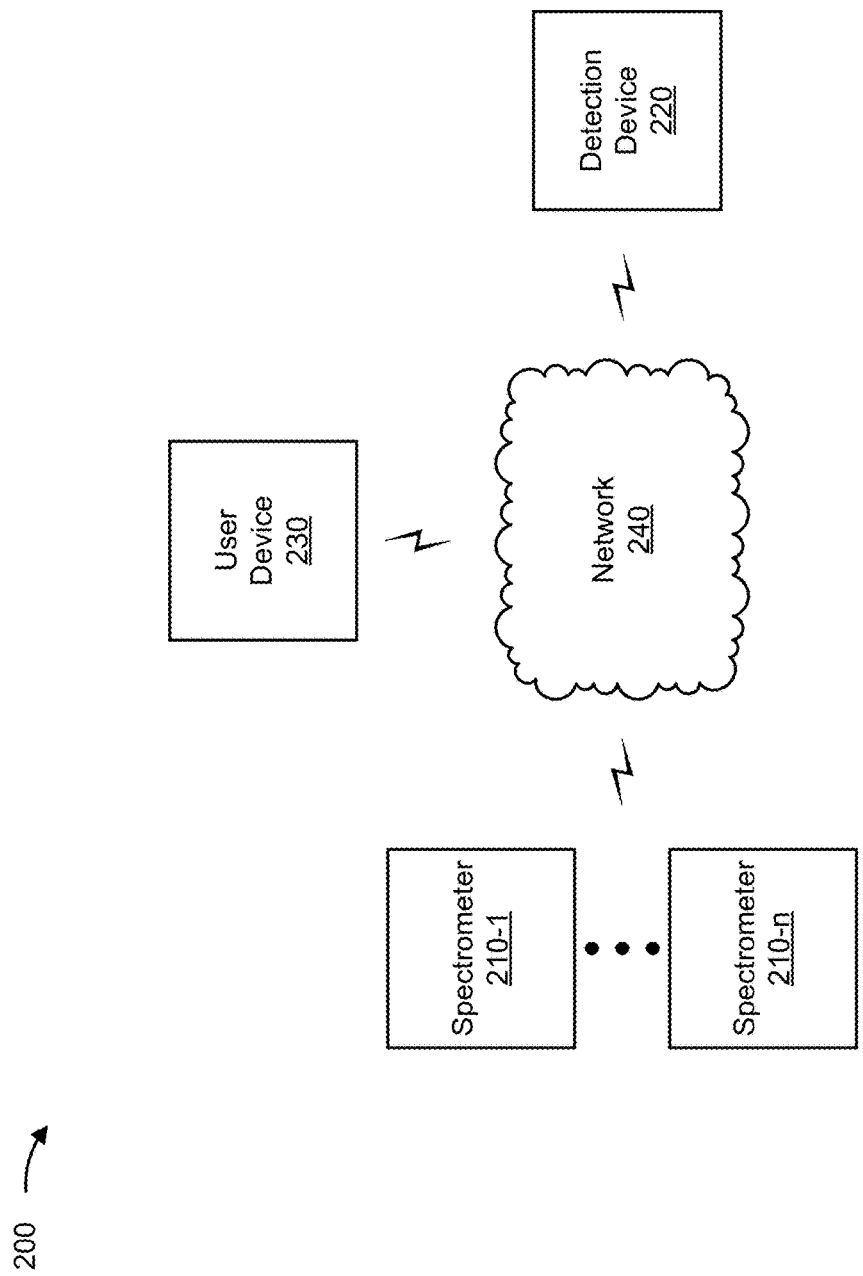
FIG. 2 is a diagram of an example environment in which systems and/or methods described herein may be implemented.

FIG. 2 is a diagram of an example environment 200 in which systems and/or methods, described herein, may be implemented. As shown in FIG. 2, environment 200 may include one or more spectrometers 210-1 through 210-n (n≥1) (herein collectively referred to as spectrometers 210, and individually as spectrometer 210), a detection device 220, a user device 230, and a network 240. Devices of environment 200 may interconnect via wired connections, wireless connections, or a combination of wired and wireless connections.

Spectrometer 210 includes a device capable of performing a spectroscopic measurement on a sample (e.g., a sample associated with a manufacturing process). For example, spectrometer 210 may include a desktop (i.e., non-handheld) spectrometer device that performs spectroscopy (e.g., vibrational spectroscopy, such as near infrared (NIR) spectroscopy, mid-infrared spectroscopy (mid-IR), Raman spectroscopy, and/or the like). In some implementations, spectrometer 210 may be capable of providing spectral data, obtained by spectrometer 210, for analysis by another device, such as detection device 220.

Detection device 220 includes one or more devices capable of performing one or more operations associated with dynamic process end point detection, as described herein. For example, detection device 220 may include a server, a group of servers, a computer, a cloud computing device, and/or the like. In some implementations, detection device 220 may receive information from and/or transmit information to another device in environment 200, such as spectrometer 210 and/or user device 230.

User device 230 includes one or more devices capable of receiving, processing, and/or providing information associated with dynamic process end point detection, as described herein. For example, user device 230 may include a communication and computing device, such as a desktop computer, a mobile phone (e.g., a smart phone, a radiotelephone, etc.), a laptop computer, a tablet computer, a handheld computer, a wearable communication device (e.g., a smart wristwatch, a pair of smart eyeglasses, etc.), or a similar type of device.

Network 240 includes one or more wired and/or wireless networks. For example, network 240 may include a cellular network (e.g., a 5G network, a 4G network, an long-term evolution (LTE) network, a 3G network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, and/or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
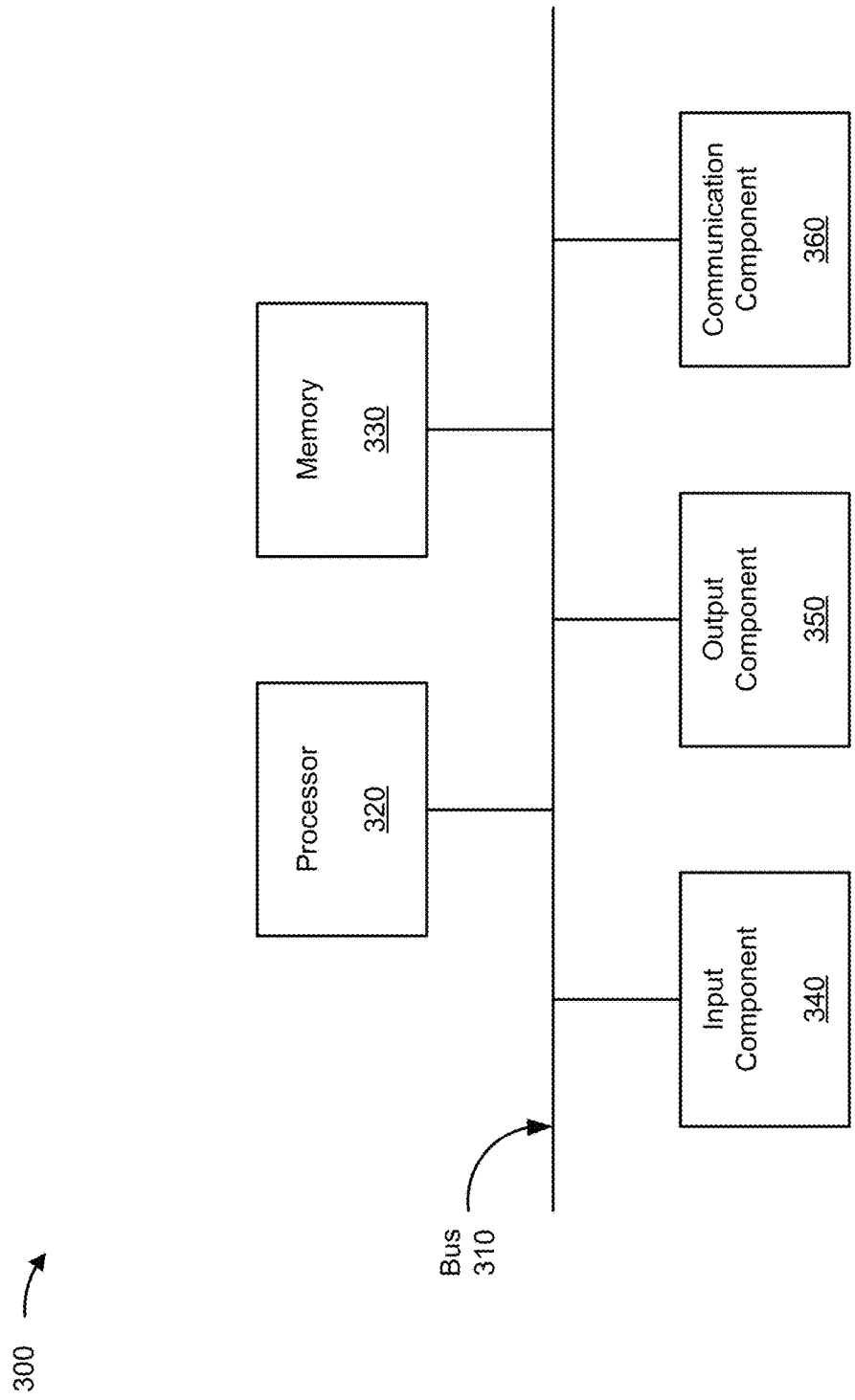
FIG. 3 is a diagram of example components of one or more devices of FIG. 2.

FIG. 3 is a diagram of example components of a device 300, which may correspond to spectrometer 210, detection device 220, and/or user device 230. In some implementations, spectrometer 210, detection device 220, and/or user device 230 may include one or more devices 300 and/or one or more components of device 300. As shown in FIG. 3, device 300 may include a bus 310, a processor 320, a memory 330, an input component 340, an output component 350, and a communication component 360.

Bus 310 includes one or more components that enable wired and/or wireless communication among the components of device 300. Bus 310 may couple together two or more components of FIG. 3, such as via operative coupling, communicative coupling, electronic coupling, and/or electric coupling. Processor 320 includes a central processing unit, a graphics processing unit, a microprocessor, a controller, a microcontroller, a digital signal processor, a field-programmable gate array, an application-specific integrated circuit, and/or another type of processing component. Processor 320 is implemented in hardware, firmware, or a combination of hardware and software. In some implementations, processor 320 includes one or more processors capable of being programmed to perform one or more operations or processes described elsewhere herein.

Memory 330 includes volatile and/or nonvolatile memory. For example, memory 330 may include random access memory (RAM), read only memory (ROM), a hard disk drive, and/or another type of memory (e.g., a flash memory, a magnetic memory, and/or an optical memory). Memory 330 may include internal memory (e.g., RAM, ROM, or a hard disk drive) and/or removable memory (e.g., removable via a universal serial bus connection). Memory 330 may be a non-transitory computer-readable medium. Memory 330 stores information, instructions, and/or software (e.g., one or more software applications) related to the operation of device 300. In some implementations, memory 330 includes one or more memories that are coupled to one or more processors (e.g., processor 320), such as via bus 310.

Input component 340 enables device 300 to receive input, such as user input and/or sensed input. For example, input component 340 may include a touch screen, a keyboard, a keypad, a mouse, a button, a microphone, a switch, a sensor, a global positioning system sensor, an accelerometer, a gyroscope, and/or an actuator. Output component 350 enables device 300 to provide output, such as via a display, a speaker, and/or a light-emitting diode. Communication component 360 enables device 300 to communicate with other devices via a wired connection and/or a wireless connection. For example, communication component 360 may include a receiver, a transmitter, a transceiver, a modem, a network interface card, and/or an antenna.

Device 300 may perform one or more operations or processes described herein. For example, a non-transitory computer-readable medium (e.g., memory 330) may store a set of instructions (e.g., one or more instructions or code) for execution by processor 320. Processor 320 may execute the set of instructions to perform one or more operations or processes described herein. In some implementations, execution of the set of instructions, by one or more processors 320, causes the one or more processors 320 and/or the device 300 to perform one or more operations or processes described herein. In some implementations, hardwired circuitry is used instead of or in combination with the instructions to perform one or more operations or processes described herein. Additionally, or alternatively, processor 320 may be configured to perform one or more operations or processes described herein. Thus, implementations described herein are not limited to any specific combination of hardware circuitry and software.

The number and arrangement of components shown in FIG. 3 are provided as an example. Device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
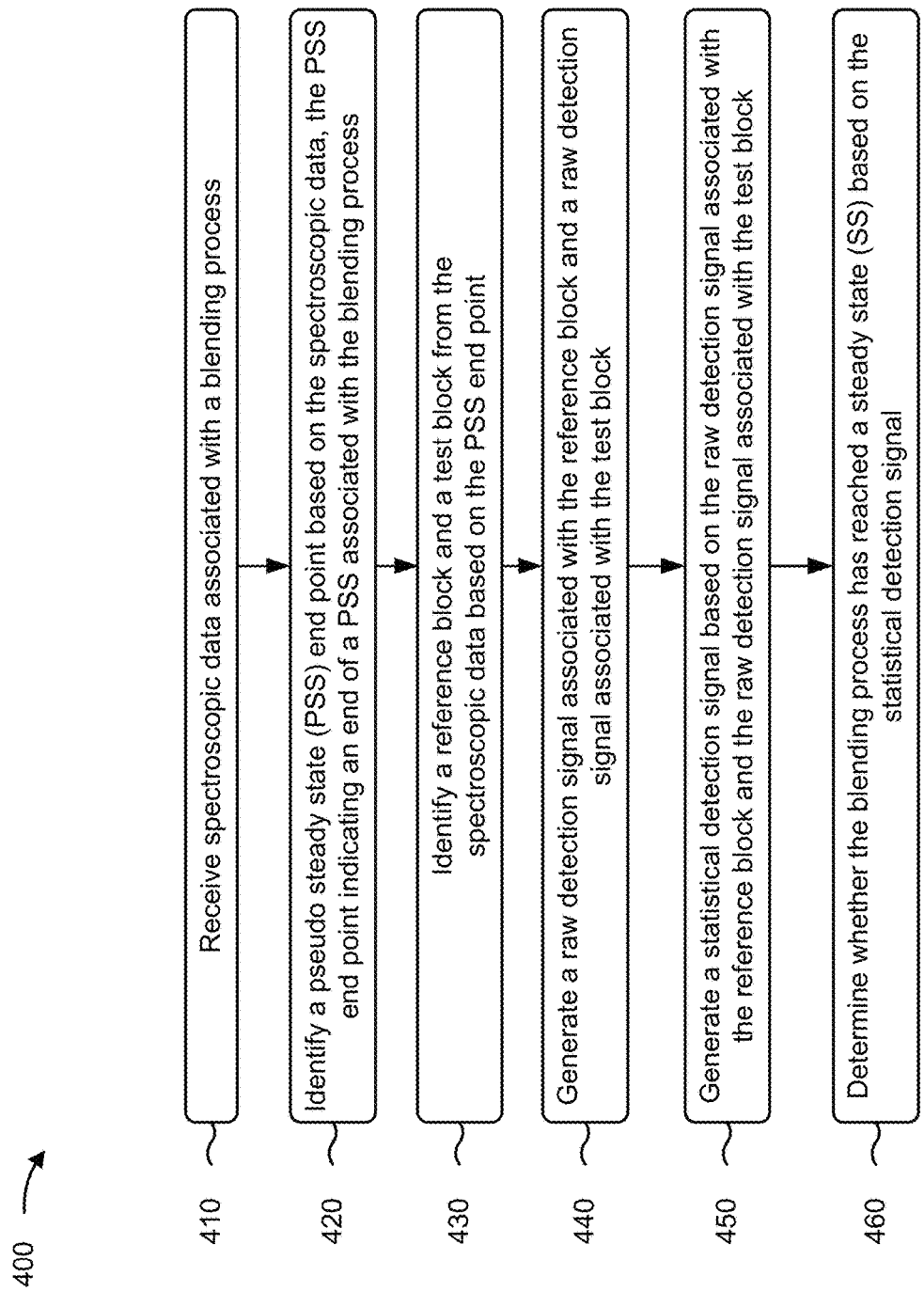

FIG. 4 is a flowchart of an example process 400 associated with dynamic process end point detection. In some implementations, one or more process blocks of FIG. 4 are performed by a detection device (e.g., detection device 220). In some implementations, one or more process blocks of FIG. 4 are performed by another device or a group of devices separate from or including the detection device, such as a spectrometer (e.g., spectrometer 210) and/or a user device (e.g., user device 230). Additionally, or alternatively, one or more process blocks of FIG. 4 may be performed by one or more components of device 300, such as processor 320, memory 330, input component 340, output component 350, and/or communication component 360.

As shown in FIG. 4, process 400 may include receiving spectroscopic data associated with a dynamic process (block 410). For example, the detection device may receive spectroscopic data associated with a blending process, as described above.

As further shown in FIG. 4, process 400 may include identifying a pseudo steady state end point based on the spectroscopic data, the pseudo steady state end point indicating an end of a pseudo steady state associated with the dynamic process (block 420). For example, the detection device may identify a pseudo steady state end point based on the spectroscopic data, the pseudo steady state end point indicating an end of a pseudo steady state associated with the blending process, as described above.

As further shown in FIG. 4, process 400 may include identifying a reference block and a test block from the spectroscopic data based on the pseudo steady state end point (block 430). For example, the detection device may identify a reference block and a test block from the spectroscopic data based on the pseudo steady state end point, as described above.

As further shown in FIG. 4, process 400 may include generating a raw detection signal associated with the reference block and a raw detection signal associated with the test block (block 440). For example, the detection device may generate a raw detection signal associated with the reference block and a raw detection signal associated with the test block, as described above.

As further shown in FIG. 4, process 400 may include generating a statistical detection signal based on the raw detection signal associated with the reference block and the raw detection signal associated with the test block (block 450). For example, the detection device may generate a statistical detection signal based on the raw detection signal associated with the reference block and the raw detection signal associated with the test block, as described above.

As further shown in FIG. 4, process 400 may include determining whether the dynamic process has reached a steady state based on the statistical detection signal (block 460). For example, the detection device may determine whether the blending process has reached a steady state based on the statistical detection signal, as described above.

Process 400 may include additional implementations, such as any single implementation or any combination of implementations described below and/or in connection with one or more other processes described elsewhere herein.

In a first implementation, identifying the pseudo steady state end point comprises performing an F-test using moving dual blocks associated with the spectroscopic data to determine a value associated with identifying the pseudo steady state end point, and determining that the value satisfies a pseudo steady state end point threshold.

In a second implementation, alone or in combination with the first implementation, the F-test is performed based on a PCA model generated based on spectra from the spectroscopic data.

In a third implementation, alone or in combination with one or more of the first and second implementations, the F-test is performed based on autoscaling whole spectrum, from the spectroscopic data, within the moving dual blocks.

In a fourth implementation, alone or in combination with one or more of the first through third implementations, the F-test is performed based on a PCA model generated based on historical spectroscopic data.

In a fifth implementation, alone or in combination with one or more of the first through fourth implementations, the raw detection signal associated with the reference block is generated based on a TSV calculated based on the reference block.

In a sixth implementation, alone or in combination with one or more of the first through fifth implementations, the raw detection signal associated with the test block is generated based on a TSV calculated based on the test block.

In a seventh implementation, alone or in combination with one or more of the first through sixth implementations, the raw detection signal associated with the reference block is generated based on an IBSD calculated based on the reference block.

In an eighth implementation, alone or in combination with one or more of the first through seventh implementations, the raw detection signal associated with the test block is generated based on an IBSD calculated based on the test block.

In a ninth implementation, alone or in combination with one or more of the first through eighth implementations, generating the statistical detection signal comprises performing an F-test based on the raw detection signal associated with the reference block versus the raw detection signal associated with the test block to determine the statistical detection signal.

In a tenth implementation, alone or in combination with one or more of the first through ninth implementations, determining whether the dynamic process has reached the steady state comprises determining whether a value of the statistical detection signal satisfies a condition associated with a steady state threshold.

In an eleventh implementation, alone or in combination with one or more of the first through tenth implementations, process 400 includes providing an indication that the dynamic process has reached the steady state based at least in part on a determination that the dynamic process has reached the steady state.

In a twelfth implementation, alone or in combination with one or more of the first through eleventh implementations, process 400 includes identifying a junction point based on the pseudo steady state end point, the junction point indicating a transition from an unsteady state to the pseudo steady state.

Although FIG. 4 shows example blocks of process 400, in some implementations, process 400 includes additional blocks, fewer blocks, different blocks, or differently arranged blocks than those depicted in FIG. 4. Additionally, or alternatively, two or more of the blocks of process 400 may be performed in parallel.

FIG. 5 is a flowchart of an example process 500 associated with dynamic process end point detection. In some implementations, one or more process blocks of FIG. 5 are performed by a detection device (e.g., detection device 220). In some implementations, one or more process blocks of FIG. 5 are performed by another device or a group of devices separate from or including the detection device, such as a spectrometer (e.g., spectrometer 210) and/or a user device (e.g., user device 230). Additionally, or alternatively, one or more process blocks of FIG. 5 may be performed by one or more components of device 300, such as processor 320, memory 330, input component 340, output component 350, and/or communication component 360.

As shown in FIG. 5, process 500 may include receiving spectroscopic data associated with a dynamic process (block 510). For example, the detection device may receive spectroscopic data associated with a blending process, as described above.

As further shown in FIG. 5, process 500 may include identifying a pseudo steady state end point based on the spectroscopic data, the pseudo steady state end point indicating an end of a pseudo steady state associated with the dynamic process (block 520). For example, the detection device may identify a pseudo steady state end point based on the spectroscopic data, the pseudo steady state end point indicating an end of a pseudo steady state associated with the blending process, as described above.

As further shown in FIG. 5, process 500 may include identifying a reference block and a test block from the spectroscopic data based on the pseudo steady state end point (block 530). For example, the detection device may identify a reference block and a test block from the spectroscopic data based on the pseudo steady state end point, as described above.

As further shown in FIG. 5, process 500 may include generating a raw detection signal associated with the reference block and a raw detection signal associated with the test block (block 540). For example, the detection device may generate a raw detection signal associated with the reference block and a raw detection signal associated with the test block, as described above.

As further shown in FIG. 5, process 500 may include generating an averaged statistical detection signal based on the raw detection signal associated with the reference block and the raw detection signal associated with the test block (block 550). For example, the detection device may generate an averaged statistical detection signal based on the raw detection signal associated with the reference block and the raw detection signal associated with the test block, as described above.

As further shown in FIG. 5, process 500 may include determining whether the dynamic process has reached a steady state based on the averaged statistical detection signal (block 560). For example, the detection device may determine whether the blending process has reached a steady state based on the averaged statistical detection signal, as described above.

Process 500 may include additional implementations, such as any single implementation or any combination of implementations described below and/or in connection with one or more other processes described elsewhere herein.

In a first implementation, generating the averaged statistical detection comprises averaging a statistical detection signal based on a number of principal components associated with the statistical detection signal.

In a second implementation, alone or in combination with one or more of the first and second implementations, the averaged statistical detection signal is an averaged p-value signal.

In a third implementation, alone or in combination with one or more of the first through third implementations, determining whether the dynamic process has reached the steady state comprises determining whether a value of the averaged statistical detection signal satisfies a condition associated with a steady state threshold.

In a fourth implementation, alone or in combination with one or more of the first through fourth implementations, the steady state threshold is a p-value threshold that is greater than or equal to approximately 0.01.

Although FIG. 5 shows example blocks of process 500, in some implementations, process 500 includes additional blocks, fewer blocks, different blocks, or differently arranged blocks than those depicted in FIG. 5. Additionally, or alternatively, two or more of the blocks of process 500 may be performed in parallel.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, not equal to the threshold, or the like.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set. As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiple of the same item.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, or a combination of related and unrelated items), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
   receiving, by a device, spectroscopic data associated with a dynamic process;
   identifying, by the device, a pseudo steady state end point based on the spectroscopic data, the pseudo steady state end point indicating an end of a pseudo steady state associated with the dynamic process;
   identifying, by the device, a reference block and a test block from the spectroscopic data based on the pseudo steady state end point;
   generating, by the device, a raw detection signal associated with the reference block and a raw detection signal associated with the test block;
   generating, by the device, an averaged statistical detection signal based on the raw detection signal associated with the reference block and the raw detection signal associated with the test block; and
   determining, by the device, whether the dynamic process has reached a steady state based on the averaged statistical detection signal.

2. The method of claim 1, wherein generating the averaged statistical detection comprises averaging a statistical detection signal based on a number of principal components associated with the statistical detection signal.

3. The method of claim 1, wherein the averaged statistical detection signal is an averaged p-value signal.

4. The method of claim 1, wherein determining whether the dynamic process has reached the steady state comprises:
   determining whether a value of the averaged statistical detection signal satisfies a condition associated with a steady state threshold.

5. The method of claim 4, wherein the steady state threshold is a p-value threshold that is greater than or equal to approximately 0.01.

6. A device, comprising:
   one or more memories; and
   one or more processors, coupled to the one or more memories, configured to:
   receive spectroscopic data associated with a dynamic process;
   identify a pseudo steady state end point based on the spectroscopic data, the pseudo steady state end point indicating an end of a pseudo steady state associated with the dynamic process;
   identify a reference block and a test block from the spectroscopic data based on the pseudo steady state end point;
   generate a raw detection signal associated with the reference block and a raw detection signal associated with the test block;
   generate an averaged statistical detection signal based on the raw detection signal associated with the reference block and the raw detection signal associated with the test block; and
   determine whether the dynamic process has reached a steady state based on the averaged statistical detection signal.

7. The device of claim 6, wherein the one or more processors, when generating the averaged statistical detection signal, are configured to average a statistical detection signal based on a number of principal components associated with the statistical detection signal.

8. The device of claim 6, wherein the averaged statistical detection signal is an averaged p-value signal.

9. The device of claim 6, wherein the one or more processors, to determine whether the dynamic process has reached the steady state, are configured to:
   determine whether a value of the averaged statistical detection signal satisfies a condition associated with a steady state threshold.

10. The device of claim 9, wherein the steady state threshold is a p-value threshold that is greater than or equal to approximately 0.01.

11. A non-transitory computer-readable medium storing a set of instructions, the set of instructions comprising:
    one or more instructions that, when executed by one or more processors of a device, cause the device to:
    receive spectroscopic data associated with a dynamic process;
    identify a pseudo steady state end point based on the spectroscopic data, the pseudo steady state end point indicating an end of a pseudo steady state associated with the dynamic process;
    identify a reference block and a test block from the spectroscopic data based on the pseudo steady state end point;
    generate a raw detection signal associated with the reference block and a raw detection signal associated with the test block;
    generate an averaged statistical detection signal based on the raw detection signal associated with the reference block and the raw detection signal associated with the test block; and
    determine whether the dynamic process has reached a steady state based on the averaged statistical detection signal.

12. The non-transitory computer-readable medium of claim 11, wherein the one or more instructions, that cause the device to generate the averaged statistical detection signal, cause the device to average a statistical detection signal based on a number of principal components associated with the statistical detection signal.

13. The non-transitory computer-readable medium of claim 11, wherein the averaged statistical detection signal is an averaged p-value signal.

14. The non-transitory computer-readable medium of claim 11, wherein the one or more instructions, that cause the device to determine whether the dynamic process has reached the steady state, cause the device to:

determine whether a value of the averaged statistical detection signal satisfies a condition associated with a steady state threshold.

15. The non-transitory computer-readable medium of claim 14, wherein the steady state threshold is a p-value threshold that is greater than or equal to approximately 0.01.

16. The method of claim 1, wherein the raw detection signal associated with the reference block is generated by calculating a travel space volume associated with the reference block.

17. The method of claim 1, wherein the raw detection signal associated with the reference block is generated by calculating an individual block standard deviation associated with the reference block.

18. The device of claim 6, wherein the one or more processors, to generate the raw detection signal associated with the test block, are configured to:
  calculate a travel space volume associated with the test block.

19. The device of claim 6, wherein the one or more processors, to generate the raw detection signal associated with the test block, are configured to:
  calculate an individual block standard deviation associated with the test block.

20. The non-transitory computer-readable medium of claim 11, wherein the one or more instructions, that cause the device to generate the raw detection signal associated with the reference block, cause the device to:
  calculate a travel space volume associated with the reference block.

* * * * *